United States Patent
Priebe et al.

(10) Patent No.: US 10,358,439 B2
(45) Date of Patent: Jul. 23, 2019

(54) DNA BINDING AGENTS WITH A MINOR GROOVE BINDING TAIL

(71) Applicants: Board of Regents, The University of Texas System, Austin, TX (US); Board of Regents, The University of Texas System, Austin, TX (US)

(72) Inventors: Waldemar Priebe, Houston, TX (US); Liwei Guo, Birmingham, AL (US); Arkadiusz Kazimierski, Old Bridge, NJ (US); Izabela Fokt, Houston, TX (US); Charles Conrad; Timothy Madden, Spring, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 15/759,884

(22) PCT Filed: Sep. 16, 2016

(86) PCT No.: PCT/US2016/052144
§ 371 (c)(1),
(2) Date: Mar. 14, 2018

(87) PCT Pub. No.: WO2017/049091
PCT Pub. Date: Mar. 23, 2017

(65) Prior Publication Data
US 2018/0251454 A1 Sep. 6, 2018

Related U.S. Application Data

(60) Provisional application No. 62/219,380, filed on Sep. 16, 2015.

(51) Int. Cl.
| | |
|---|---|
| C07C 13/66 | (2006.01) |
| C07D 309/14 | (2006.01) |
| C07D 405/12 | (2006.01) |
| C07D 405/14 | (2006.01) |
| C07H 15/24 | (2006.01) |
| C07H 15/244 | (2006.01) |
| A61P 35/00 | (2006.01) |

(52) U.S. Cl.
CPC ............ *C07D 405/14* (2013.01); *A61P 35/00* (2018.01); *C07C 13/66* (2013.01); *C07D 309/14* (2013.01); *C07D 405/12* (2013.01); *C07H 15/24* (2013.01); *C07H 15/244* (2013.01)

(58) Field of Classification Search
CPC .... C07C 13/66; C07D 309/14; C07D 405/12; C07D 405/14; C07H 15/24; C07H 15/244
See application file for complete search history.

(56) References Cited

U.S. PATENT DOCUMENTS

| | | | |
|---|---|---|---|
| 4,196,127 | A | 4/1980 | Johnson et al. |
| 4,288,608 | A | 9/1981 | Johnson et al. |
| 4,591,636 | A | 5/1986 | Broadhurst et al. |
| 6,673,907 | B2 | 1/2004 | Priebe et al. |
| 7,109,177 | B2 | 9/2006 | Priebe et al. |
| 7,557,090 | B2 | 7/2009 | Priebe et al. |

FOREIGN PATENT DOCUMENTS

| | | |
|---|---|---|
| WO | WO 2003/072058 | 9/2003 |
| WO | WO 2008/029294 | 3/2008 |

OTHER PUBLICATIONS

Bickel et al., "Delivery of peptides and proteins through the blood-brain barrier," *Adv. Drug Deliv. Rev.*, 46:247-279, 2001.
International Preliminary Report on Patentability issued in corresponding PCT Application No. PCT/US2016/052144, dated Mar. 29, 2018.
International Search Report and Written Opinion issued in corresponding PCT Application No. PCT/US2016/052144, dated Feb. 3, 2017.
Pardridge, "Blood-brain barrier biology and methodology," *Neurovirol.*, 5:556-569, 1999.
PubChem Substance Record for SID 53581774, <URL:http://pubchem.ncbi.nlm.nih.gov/substance/53581774>, 2008.
Database Accession No. 2000:461545, Chemical Abstracts Service, 2000.
Extended European Search Report issued in European Application No. 16847389.0, dated Feb. 26, 2019.
Wang et al., "Doxorubicin and DNA minor groove-binding oligopeptide conjugates as anticancer agents," Gene, 149(1):63-67, 1994.

*Primary Examiner* — Laura L Stockton
(74) *Attorney, Agent, or Firm* — Parker Highlander PLLC

(57) ABSTRACT

Provided herein are compounds which intercalate into the DNA of a cell and are capable of crossing the blood brain barrier of a formula provided herein. Pharmaceutical compositions of the compounds and methods of treating cancer, for example brain, lung, or pancreatic cancer, are also provided herein.

20 Claims, 4 Drawing Sheets

A.
B.
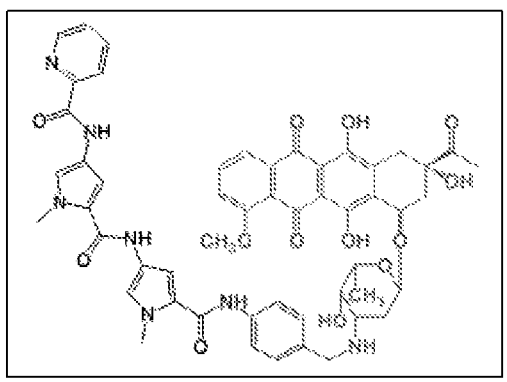
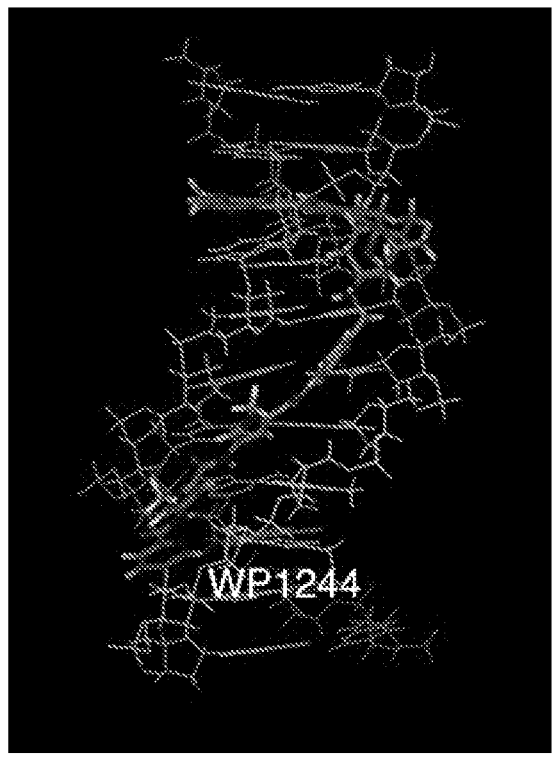
FIGS. 1A-B

FIGS. 4A-B

DNA BINDING AGENTS WITH A MINOR GROOVE BINDING TAIL

The present application is a national phase application under 35 U.S.C. § 371 of International Application No. PCT/US2016/052144, filed Sep. 16, 2016, which claims the priority benefit of U.S. provisional application No. 62/219,380, filed Sep. 16, 2015, the entire contents of each of which are incorporated herein by reference.

BACKGROUND OF THE INVENTION

1. Field of the Invention

The present invention relates generally to the field of medicinal chemistry. More particularly, it concerns chemotherapeutic compounds capable of binding to DNA and/or crossing the blood brain barrier.

2. Description of Related Art

The anthracyclines daunorubicin and doxorubicin (DOX) are some of the more commonly used chemotherapeutic antibiotics. The anthracyclines achieve their cytotoxic effect by several mechanisms, including inhibition of topoisomerase II; intercalation between DNA strands, thereby interfering with DNA and RNA synthesis; production of free radicals that react with and damage intracellular proteins and nucleic acids; chelation of divalent cations; and reaction with cell membranes. The wide range of potential sites of action may account for the broad efficacy as well as the toxicity of the anthracyclines (Young et al., 1985). Although there are marked differences in the clinical use of daunorubicin and doxorubicin, their chemical structures differ only by a single hydroxyl group on $C_{14}$. Previous modifications of these compounds have been undertaken to improve their selectivity towards specific tumors types (U.S. Pat. Nos. 6,673,907, 7,109,177, and 7,557,090 and PCT Publication WO 2008/029294). In particular, brain cancers can be difficult to treat as many compounds cannot easily cross the blood brain barrier (Pardridge, 1999; Bickel, et al., 2001). As such, new compounds which show increased activity and/or ability to cross the blood brain barrier are clinically needed.

SUMMARY OF THE INVENTION

In some aspects, the present disclosure provides new DNA binding agents with an anthracycline core and a long amine containing tail. In some aspects, the present disclosure provides compounds of the formula:

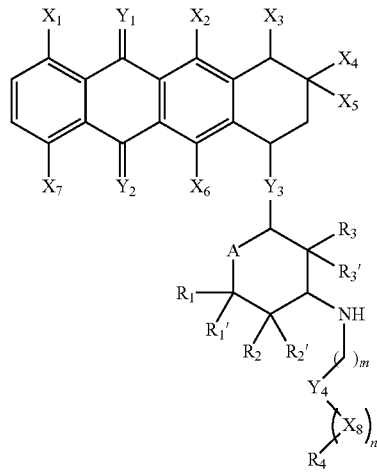

wherein:
$X_1$, $X_2$, $X_3$, $X_6$, and $X_7$ are each independently hydrogen, halo, hydroxy, carboxy, ester$_{(C \leq 12)}$, substituted ester$_{(C \leq 12)}$, alkoxy$_{(C \leq 12)}$, or substituted alkoxy$_{(C \leq 12)}$;
$X_4$ is acyl$_{(C \leq 18)}$ or substituted acyl$_{(C \leq 18)}$;
$X_5$ is hydrogen, hydroxy, alkoxy$_{(C \leq 12)}$, or substituted alkoxy$_{(C \leq 12)}$;
$Y_1$, $Y_2$, and $Y_3$ are each independently O, S, or NH;
A is O or S;
$R_1$, $R_1'$, $R_2$, $R_2'$, $R_3$, and $R_3'$ are each independently hydrogen, amino, halo, hydroxy, mercapto, or alkyl$_{(C \leq 8)}$, alkoxy$_{(C \leq 8)}$, alkylthio$_{(C \leq 8)}$, alkylamino$_{(C \leq 8)}$, dialkylamino$_{(C \leq 8)}$, or a substituted version of any of these groups;
$Y_4$ is arenediyl$_{(C \leq 12)}$, heteroarenediyl$_{(C \leq 12)}$, or a substituted version of either of these groups;
each $X_8$ is independently —$X_9$-heteroarenediyl$_{(C \leq 12)}$ or substituted —$X_9$heteroarenediyl$_{(C \leq 12)}$, wherein:
$X_9$ is —NHC(O)— or —C(O)NH—;
$R_4$ is hydrogen, amino, nitro, alkylamino$_{(C \leq 12)}$, dialkylamino$_{(C \leq 12)}$, amido$_{(C \leq 12)}$, substituted alkylamino$_{(C \leq 12)}$, substituted dialkylamino$_{(C \leq 12)}$, or substituted amido$_{(C \leq 12)}$;
m is 0, 1, 2, or 3; and
n is 1, 2, or 3;
or a pharmaceutically acceptable salt thereof. In some embodiments, the formula is further defined as:

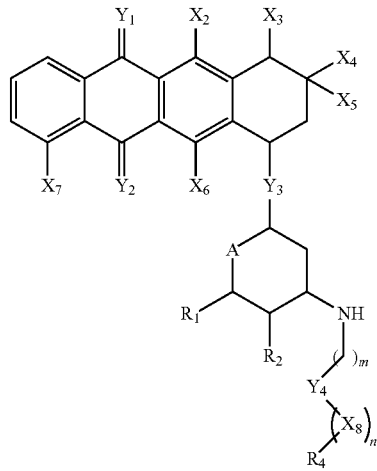

wherein:
$X_2$, $X_3$, $X_6$, and $X_7$ are each independently hydrogen, halo, hydroxy, carboxy, ester$_{(C \leq 12)}$, substituted ester$_{(C \leq 12)}$, alkoxy$_{(C \leq 12)}$, or substituted alkoxy$_{(C \leq 12)}$;
$X_4$ is acyl$_{(C \leq 18)}$ or substituted acyl$_{(C \leq 18)}$;
$X_5$ is hydrogen, hydroxy, alkoxy$_{(C \leq 12)}$, or substituted alkoxy$_{(C \leq 12)}$;
$Y_1$, $Y_2$, and $Y_3$ are each independently O, S, or NH;
A is O or S;
$R_1$ and $R_2$ are each independently hydrogen, amino, halo, hydroxy, mercapto, or alkyl$_{(C \leq 8)}$, alkoxy$_{(C \leq 8)}$, alkylthio$_{(C \leq 8)}$, alkylamino$_{(C \leq 8)}$, dialkylamino$_{(C \leq 8)}$, or a substituted version of any of these groups;
$Y_4$ is arenediyl$_{(C \leq 12)}$, heteroarenediyl$_{(C \leq 12)}$, or a substituted version of either of these groups;
each $X_8$ is independently —$X_9$-heteroarenediyl$_{(C \leq 12)}$ or substituted —$X_9$-heteroarenediyl$_{(C \leq 12)}$, wherein:
$X_9$ is —NHC(O)— or —C(O)NH—;

R₄ is hydrogen, amino, nitro, alkylamino$_{(C≤12)}$, dialkylamino$_{(C≤12)}$, amido$_{(C≤12)}$, substituted alkylamino$_{(C≤12)}$, substituted dialkylamino$_{(C≤12)}$, or substituted amido$_{(C≤12)}$;

m is 0, 1, 2, or 3; and n is 1, 2, or 3;

or a pharmaceutically acceptable salt thereof. In some embodiments, the formula is further defined as:

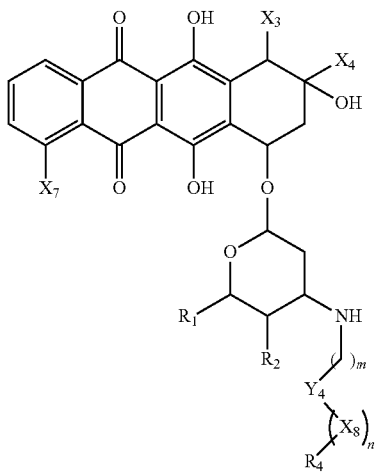

wherein:
X₇ is hydrogen, halo, hydroxy, carboxy, alkoxy$_{(C≤12)}$, substituted alkoxy$_{(C≤12)}$, ester$_{(C≤12)}$, substituted ester$_{(C≤12)}$;

X₄ is acyl$_{(C≤18)}$ or substituted acyl$_{(C≤18)}$;

R₁ and R₂ are each independently hydrogen, amino, halo, hydroxy, mercapto, or alkyl$_{(C≤8)}$, alkoxy$_{(C≤8)}$, alkylthio$_{(C≤8)}$, alkylamino$_{(C≤8)}$, dialkylamino$_{(C≤8)}$, or a substituted version of any of these groups;

Y₄ is a covalent bond, arenediyl$_{(C≤12)}$, heteroarenediyl$_{(C≤12)}$, or a substituted version of either of these groups;

each X₈ is independently —X₉-heteroarenediyl$_{(C≤12)}$ or substituted —X₉-heteroarenediyl$_{(C≤12)}$, wherein:

X₉ is —NHC(O)— or —C(O)NH—;

R₄ is hydrogen, amino, nitro, alkylamino$_{(C≤12)}$, dialkylamino$_{(C≤12)}$, amido$_{(C≤12)}$, substituted alkylamino$_{(C≤12)}$, substituted dialkylamino$_{(C≤12)}$, or substituted amido$_{(C≤12)}$;

m is 0, 1, 2, or 3; and n is 1, 2, or 3;

or a pharmaceutically acceptable salt thereof.

In some embodiments, X₇ is alkoxy$_{(C≤12)}$ or substituted alkoxy$_{(C≤12)}$ such as X₇ is methoxy. In other embodiments, X₇ is halo such as fluoro. In some embodiments, X₄ is acyl$_{(C≤18)}$ or substituted acyl$_{(C≤18)}$. In some embodiments, X₄ is acyl$_{(C≤8)}$ such as —C(O)CH₃. In other embodiments, X₄ is substituted acyl$_{(C≤8)}$ such as C(O)CH₂OH. In some embodiments, R₁ is alkyl$_{(C≤8)}$ such as methyl. In other embodiments, R₁ is substituted alkyl$_{(C≤8)}$ such as fluoromethyl, difluoromethyl, trifluoromethyl, or hydroxymethyl. In some embodiments, R₂ is hydroxy. In some embodiments, m is 1. In some embodiments, Y₄ is arenediyl$_{(C≤12)}$ such as benzenediyl. In other embodiments, Y₄ is a covalent bond.

In some embodiments, X₈ is —X₉-heteroarenediyl$_{(C≤12)}$. In some embodiments, X₈ is —NHC(O)-heteroarenediyl$_{(C≤12)}$. In some embodiments, the heteroarenediyl$_{(C≤12)}$ of X₈ is 2,5-pyridindiyl, 2,4-pyrroldiyl, or 2,4-N-methylpyrroldiyl. In some embodiments, X₈ is:

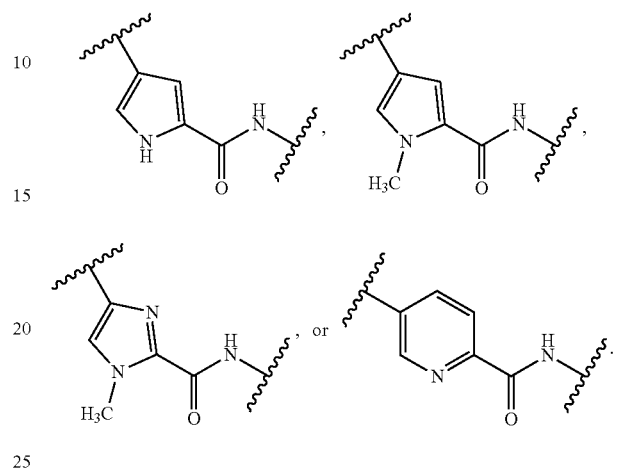

In some embodiments, X₈ is:

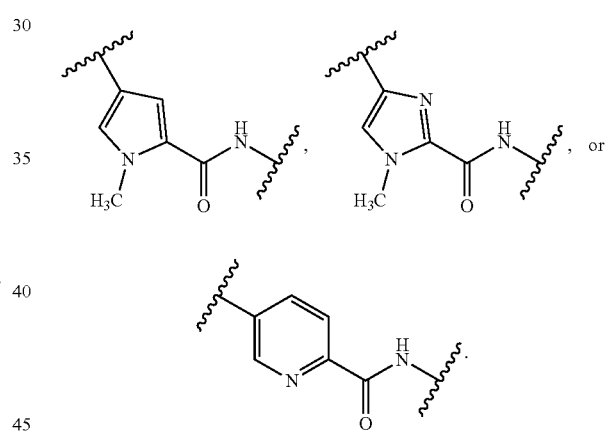

In some embodiments, X₈ is:

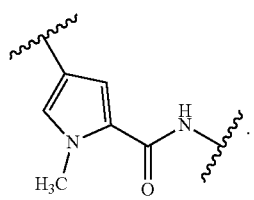 [SMILES: *NC(=O)c1cc(*)cn1C]

In some embodiments, R₄ is hydrogen. In other embodiments, R₄ is nitro. In other embodiments, R₄ is amido$_{(C≤12)}$ such as —NHC(O)H. In some embodiments, the compounds are formulated as a pharmaceutically acceptable salt. In some embodiments, the compounds are formulated as a mineral acid addition salt. In some embodiments, the compounds are formulated as an HCl acid salt. In some embodiments, the compounds re further defined as:

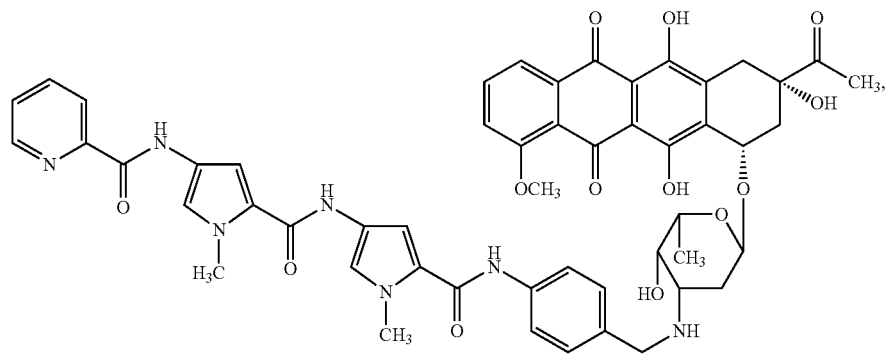
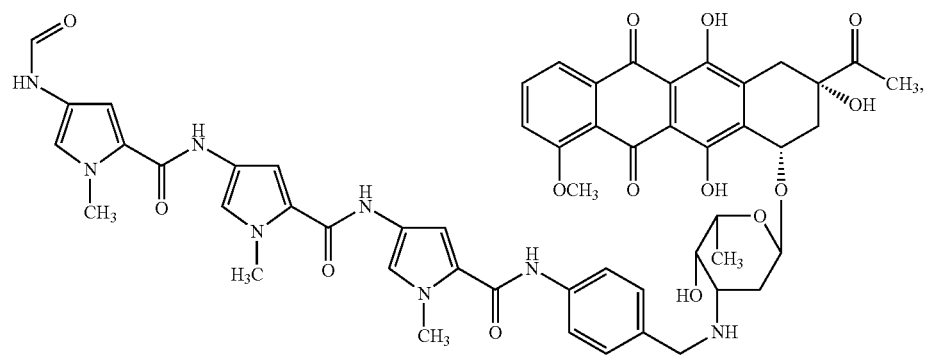
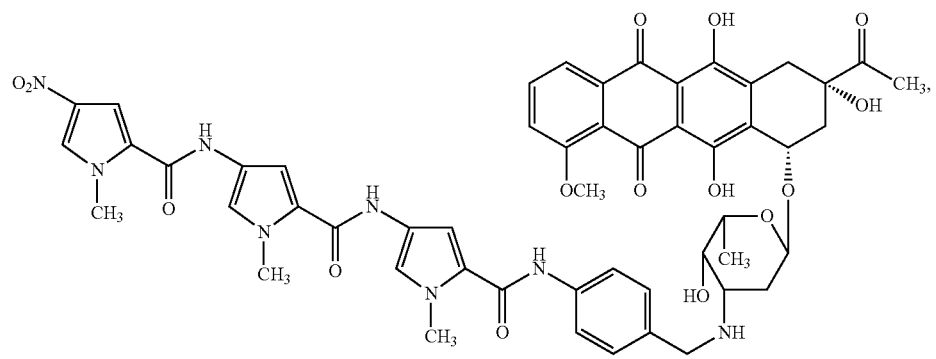
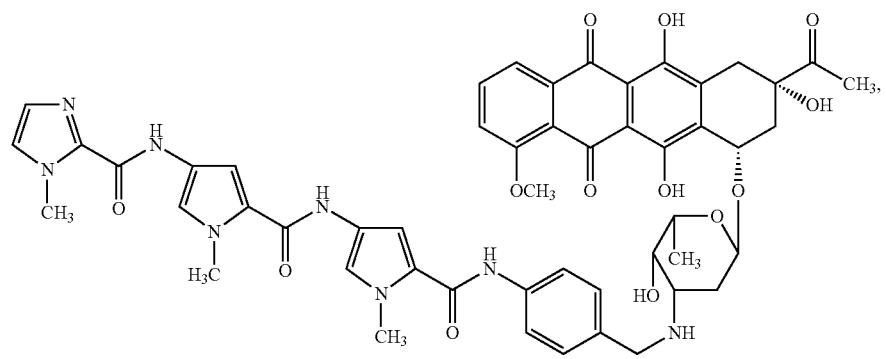

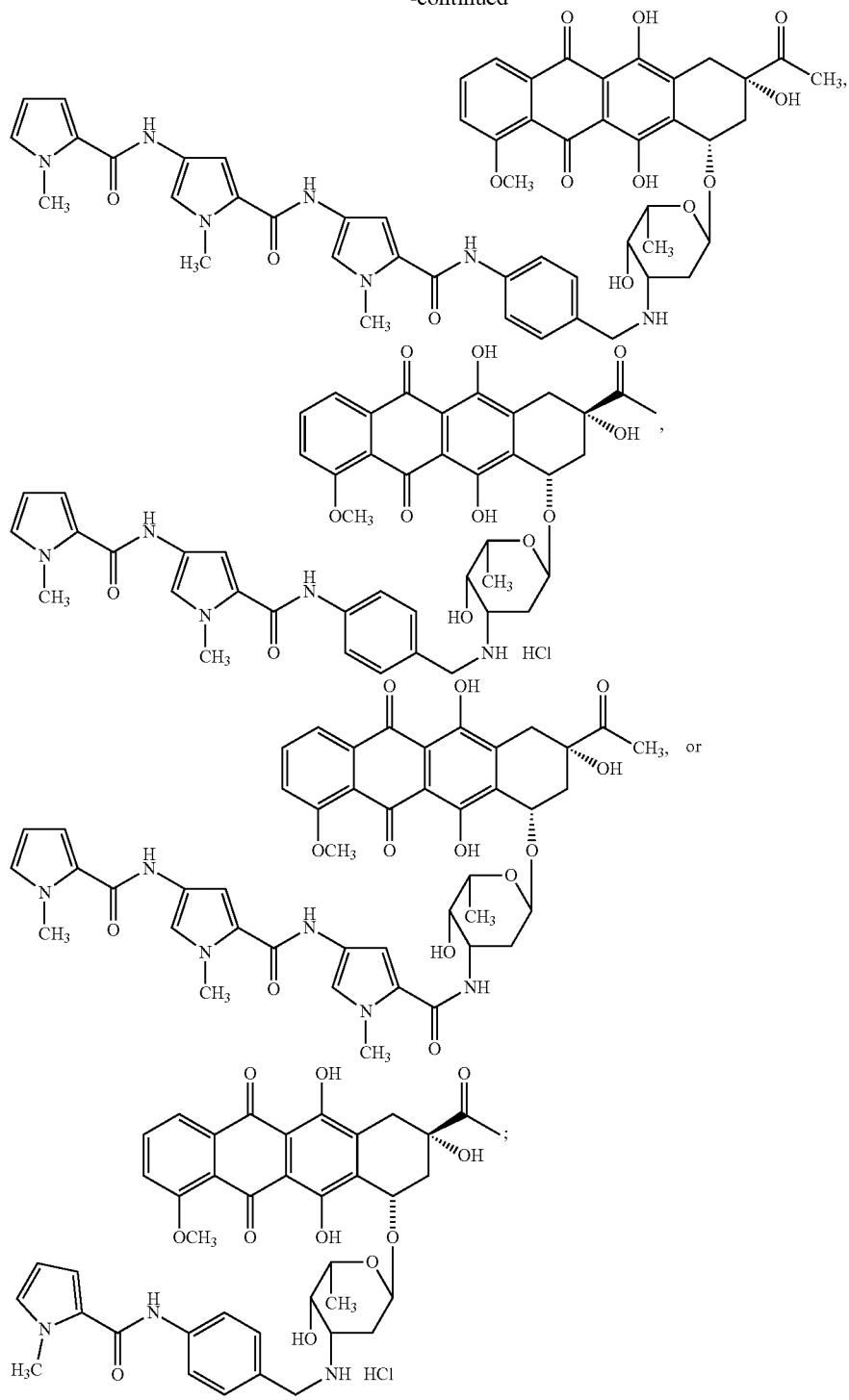

or a pharmaceutically acceptable salt thereof.

In yet another aspect, the present disclosure provides pharmaceutical compositions comprising:
(a) a compound described herein; and
(b) a pharmaceutically acceptable carrier.

In some embodiments, the pharmaceutical compositions are formulated for intraarterial, intravenous, or oral administration. In some embodiments, the pharmaceutical compositions are formulated as a unit dose.

In still yet another aspects, the present disclosure provides method of treating cancer in a patient comprising administering a therapeutically effective amount of a compound or composition described herein to the patient in need thereof. In some embodiments, the cancer is a cancer of the of the bladder, blood, bone, brain, breast, central nervous system, cervix, colon, endometrium, esophagus, gall bladder, gastrointestinal tract, genitalia, genitourinary tract, head, kidney, larynx, liver, lung, muscle tissue, neck, oral or nasal mucosa, ovary, pancreas, prostate, skin, spleen, small intestine, large intestine, stomach, testicle, or thyroid. In some embodiments, the cancer is lung cancer, brain cancer, or pancreatic cancer. In some embodiments, the cancer is brain cancer such as a glioblastoma or a metastasis to the brain. In some embodiments, the cancer is a metastasis to the brain by melanoma, lymphoma, breast, or lung cancer. In some embodiments, the compounds or compositions cross the blood-brain barrier. In some embodiments, the methods comprise administering the compound systemically and allowing the compound to penetrate the brain by diffusion across the blood brain barrier. In some embodiments, the methods comprise administering a second anti-cancer therapy. In some embodiments, the second anti-cancer therapy is a second chemotherapeutic compound, radiation therapy, surgery, or immunotherapy. In some embodiments, the patient is a mammal. In some embodiments, the patient is a human. In some embodiments, the methods comprise administering the compound once. In other embodiments, the methods comprise administering the compound two or more times.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIGS. 1A-B—(A) Structure of compound WP1244 incorporating anthracycline and distamycin fragments (U87-MG brain tumor $IC_{50}$ of 0.2 nM) and (B) its proposed complex with DNA.

DESCRIPTION OF ILLUSTRATIVE EMBODIMENTS

Figure 2:
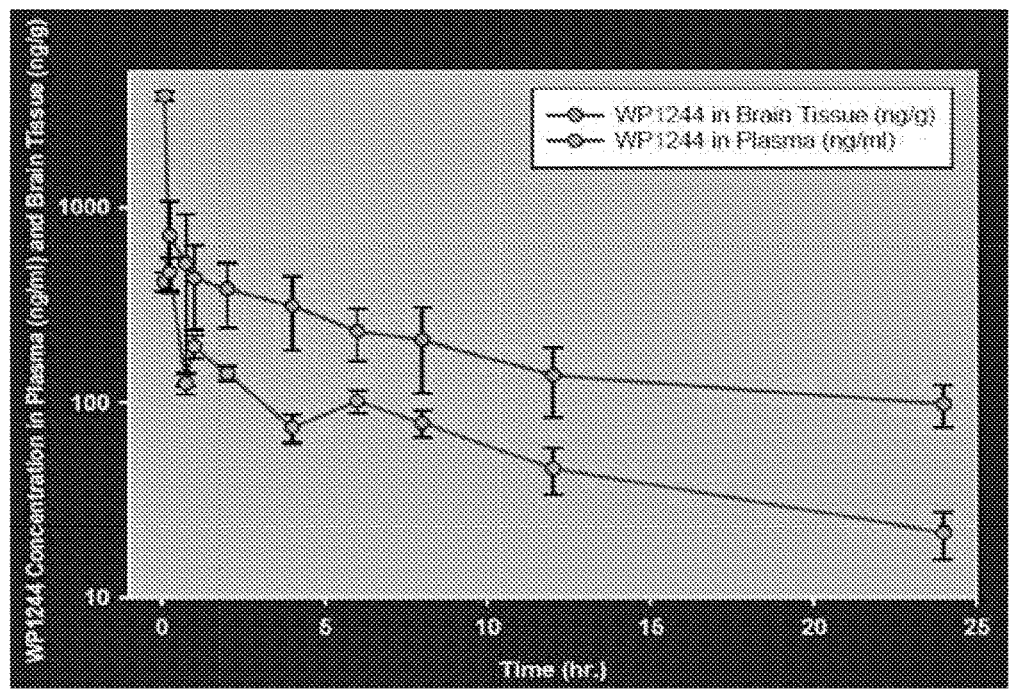
FIG. 2—WP1244 Mouse Plasma Pharmacokinetics and Brain Tissue Biodistribution after 10 mg/kg IV dose (0-24 hr).

The present disclosure provides compounds which may be used to treat cancer and/or bind to DNA. Without wishing to be bound by any theory, it is believed that the anthracycline moiety intercalates into the DNA helix and the polyamine tail binds the phosphate backbone. In some embodiments, the compounds described herein show increased permeability across the blood brain barrier allowing the compounds to penetrate into brain tissue. The compounds provided herein may be used to treat cancer especially cancers of the brain, lungs, and pancreas.

I. Compounds of the Present Invention

The compounds provided by the present disclosure are shown, for example, above in the summary of the invention section and in the claims below. They may be made using the methods outlined in the Examples section. These methods can be further modified and optimized using the principles and techniques of organic chemistry as applied by a person skilled in the art. Such principles and techniques are taught, for example, in March's Advanced Organic Chemistry: Reactions, Mechanisms, and Structure (2007), which is incorporated by reference herein.

Compounds of the disclosure may contain one or more asymmetrically-substituted carbon or nitrogen atoms, and may be isolated in optically active or racemic form. Thus, all chiral, diastereomeric, racemic form, epimeric form, and all geometric isomeric forms of a chemical formula are intended, unless the specific stereochemistry or isomeric form is specifically indicated. Compounds may occur as racemates and racemic mixtures, single enantiomers, diastereomeric mixtures and individual diastereomers. In some embodiments, a single diastereomer is obtained. The chiral centers of the compounds of the present disclosure can have the S or the R configuration.

Chemical formulas used to represent compounds of the disclosure will typically only show one of possibly several different tautomers. For example, many types of ketone groups are known to exist in equilibrium with corresponding enol groups. Similarly, many types of imine groups exist in equilibrium with enamine groups. Regardless of which tautomer is depicted for a given compound, and regardless of which one is most prevalent, all tautomers of a given chemical formula are intended.

Compounds of the disclosure may also have the advantage that they may be more efficacious than, be less toxic than, be longer acting than, be more potent than, produce fewer side effects than, be more easily absorbed than, and/or have a better pharmacokinetic profile (e.g., higher oral bioavailability and/or lower clearance) than, and/or have other useful pharmacological, physical, or chemical properties over, compounds known in the prior art, whether for use in the indications stated herein or otherwise.

In addition, atoms making up the compounds of the present disclosure are intended to include all isotopic forms of such atoms. Isotopes, as used herein, include those atoms having the same atomic number but different mass numbers. By way of general example and without limitation, isotopes of hydrogen include tritium and deuterium, and isotopes of carbon include $^{13}C$ and $^{14}C$.

Compounds of the present disclosure may also exist in prodrug form. Since prodrugs are known to enhance numerous desirable qualities of pharmaceuticals (e.g., solubility, bioavailability, manufacturing, etc.), the compounds employed in some methods of the invention may, if desired, be delivered in prodrug form. Thus, the disclosure contemplates prodrugs of compounds of the present disclosure as well as methods of delivering prodrugs. Prodrugs of the compounds employed in the disclosure may be prepared by modifying functional groups present in the compound in such a way that the modifications are cleaved, either in routine manipulation or in vivo, to the parent compound. Accordingly, prodrugs include, for example, compounds described herein in which a hydroxy, amino, or carboxy group is bonded to any group that, when the prodrug is administered to a subject, cleaves to form a hydroxy, amino, or carboxylic acid, respectively.

It should be recognized that the particular anion or cation forming a part of any salt form of a compound provided herein is not critical, so long as the salt, as a whole, is pharmacologically acceptable. Additional examples of pharmaceutically acceptable salts and their methods of preparation and use are presented in *Handbook of Pharmaceutical Salts: Properties, and Use* (2002), which is incorporated herein by reference.

It will appreciated that many organic compounds can form complexes with solvents in which they are reacted or from which they are precipitated or crystallized. These complexes are known as "solvates." Where the solvent is water, the complex is known as a "hydrate." It will also be appreciated that many organic compounds can exist in more than one solid form, including crystalline and amorphous forms. All solid forms of the compounds provided herein, including any solvates thereof are within the scope of the present disclosure.

II. Cancer and other Hyperproliferative Diseases

While hyperproliferative diseases can be associated with any disease which causes a cell to begin to reproduce uncontrollably, the prototypical example is cancer. One of the key elements of cancer is that the cell's normal apoptotic cycle is interrupted and thus agents that decreases cell counts may be used as therapeutic agents for treating these diseases. In this disclosure, the compounds described herein may be used to kill or inhibit the growth of a cancer cell (e.g., leading to decreased cancer cell counts) or a hyperproliferative cell and may be used to treat a variety of cancers including cancers of the brain, lungs, and pancreas. In some embodiments, the compounds may be used to treat brain cancer such as a glioma.

Cancer cells that may be treated with the compounds of the present disclosure include but are not limited to cells from the bladder, blood, bone, bone marrow, brain, breast, colon, esophagus, gastrointestine, gum, head, kidney, liver, lung, nasopharynx, neck, ovary, prostate, skin, stomach, pancreas, testis, tongue, cervix, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; Leydig cell tumor, malignant; lipid cell tumor, malignant; paraganglioma, malignant; extramammary paraganglioma, malignant; pheochromocytoma; glomangiosarcoma; malignant melanoma; amelanotic melanoma; superficial spreading melanoma; malignant melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; Mullerian mixed tumor; nephroblastoma; hepatoblastoma; carcinosarcoma; mesenchymoma, malignant; Brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; Kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; Ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia. In certain aspects, the tumor may comprise an osteosarcoma, angiosarcoma, rhabdosarcoma, leiomyosarcoma, Ewing sarcoma, glioblastoma, neuroblastoma, or leukemia.

III. Pharmaceutical Compositions and Therapeutic Administration

A. Pharmaceutical Compositions and Preparations

Where clinical applications are contemplated, it will be necessary to prepare pharmaceutical compositions in a form appropriate for the intended application. In some embodiments, such formulation with the compounds of the present disclosure is contemplated. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refers to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. Such routes include oral, nasal, buccal, rectal, vaginal, urethral, or topical route. Alternatively, administration may be by orthotopic, intradermal, subcutaneous, intramuscular, intratumoral, intraperitoneal, or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compounds described herein may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present disclosure may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 mL of isotonic NaCl solution and either added to 1000 mL of hypodermoclysis fluid or injected at the proposed site of infusion, (see for example, "Remington's Pharmaceutical Sciences," 15th Edition, pages 1035-1038 and 1570-1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

B. Methods of Treatment

In particular, the compositions that may be used in treating cancer in a patient (e.g., a human subject) are disclosed herein. The compositions described above are preferably administered to a mammal (e.g., rodent, human, non-human primates, canine, bovine, ovine, equine, feline, etc.) in an effective amount, that is, an amount capable of producing a desirable result in a treated subject (e.g., causing apoptosis of cancerous cells). Toxicity and therapeutic efficacy of the compositions utilized in methods of the invention can be determined by standard pharmaceutical procedures. As is well known in the medical and veterinary arts, dosage for any one animal depends on many factors, including the subject's size, body surface area, body weight, age, the particular composition to be administered, time and route of administration, general health, the clinical symptoms of the cancer and other drugs being administered concurrently. A composition as described herein is typically administered at a dosage that induces death of cancerous cells (e.g., induces apoptosis of a cancer cell), as assayed by identifying a reduction in hematological parameters (complete blood count—CBC), or cancer cell growth or proliferation. In some embodiments, amounts of the compounds used to treat the cancer is calculated to be from about 0.01 mg to about 10,000 mg/day. In some embodiments, the amount is from about 1 mg to about 1,000 mg/day. In some embodiments, these dosings may be reduced or increased based upon the biological factors of a particular patient such as increased or decreased metabolic breakdown of the drug or decreased uptake by the digestive tract if administered orally. Additionally, the compounds may be more efficacious and thus a smaller dose is required to achieve a similar effect. Such a dose is typically administered once a day for a few weeks or until sufficient reducing in cancer cells has been achieved.

The therapeutic methods of the invention (which include prophylactic treatment) in general include administration of a therapeutically effective amount of the compositions described herein to a subject in need thereof, including a mammal, particularly a human. Such treatment will be suitably administered to subjects, particularly humans, suffering from, having, susceptible to, or at risk for a disease, disorder, or symptom thereof. Determination of those subjects "at risk" can be made by any objective or subjective determination by a diagnostic test or opinion of a subject or health care provider (e.g., genetic test, enzyme or protein marker, marker (as defined herein), family history, and the like).

IV. Combination Therapies

It is envisioned that the compounds described herein may be used in combination therapies with an additional chemotherapeutic agent or a compound which mitigates one or more of the side effects experienced by the patient.

Furthermore, it is very common in the field of cancer therapy to combine therapeutic modalities. The following is a general discussion of therapies that may be used in conjunction with the therapies of the present disclosure.

To treat cancers using the methods and compositions of the present disclosure, one would generally contact a tumor cell or subject with a compound and at least one other therapy. These therapies would be provided in a combined amount effective to achieve a reduction in one or more disease parameter. This process may involve contacting the cells/subjects with the both agents/therapies at the same time, e.g., using a single composition or pharmacological formulation that includes both agents, or by contacting the cell/subject with two distinct compositions or formulations, at the same time, wherein one composition includes the compound and the other includes the other agent.

Alternatively, the compounds described herein may precede or follow the other treatment by intervals ranging from minutes to weeks. One would generally ensure that a significant period of time did not expire between the time of each delivery, such that the therapies would still be able to exert an advantageously combined effect on the cell/subject. In such instances, it is contemplated that one would contact the cell with both modalities within about 12-24 hours of each other, within about 6-12 hours of each other, or with a delay time of only about 1-2 hours. In some situations, it may be desirable to extend the time period for treatment significantly; however, where several days (2, 3, 4, 5, 6 or 7) to several weeks (1, 2, 3, 4, 5, 6, 7 or 8) lapse between the respective administrations.

It also is conceivable that more than one administration of either the compound or the other therapy will be desired. Various combinations may be employed, where a compound of the present disclosure is "A," and the other therapy is "B," as exemplified below:

A/B/A B/A/B B/B/A A/A/B B/A/A A/B/B B/B/B/A B/B/A/B
A/A/B/B A/B/A/B A/B/B/A B/B/A/A B/A/B/A B/A/A/B B/B/B/A
A/A/A/B B/A/A/A A/B/A/A A/A/B/A A/B/B/B B/A/B/B B/B/A/B

Other combinations are also contemplated. Additionally, the combination therapy may comprise treating the patient with the compounds provided herein and either radiotherapy or surgery. Other combination therapies may include the compounds provided herein and one or more additional chemotherapeutic compounds. A general discussion of potential chemotherapeutic co-therapies is included below.

A. Chemotherapy

The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

Examples of chemotherapeutic agents include alkylating agents such as thiotepa and cyclosphosphamide; alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphoramide and trimethylol melamine; acetogenins (especially bullatacin and bullatacinone); a camptothecin (including the synthetic analogue topotecan); bryostatin; callystatin; CC-1065 (including its adozelesin, carzelesin and bizelesin synthetic analogues); cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin γ1 and calicheamicin ω1; dynemicin, including dynemicin A uncialamycin and derivatives thereof; bisphosphonates, such as clodronate; an esperamicin; as well as neocarzinostatin chromophore and related chromoprotein enediyne antiobiotic chromophores, aclacinomycins, actinomycin, authrarnycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including morpholino-doxorubicin, cyanomorpholino-doxorubicin, 2-pyrrolino-doxorubicin and deoxydoxorubicin), epirubicin, esorubicin, idarubicin, marcellomycin, mitomycins such as mitomycin C, mycophenolic acid, nogalarnycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as folinic acid; aceglatone; aldophosphamide glycoside; aminolevulinic acid; eniluracil; amsacrine; bestrabucil; bisantrene; edatraxate; defofamine; demecolcine; diaziquone; elformithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK polysaccharide complex); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; taxoids, e.g., paclitaxel and docetaxel; chlorambucil; gemcitabine; 6-thioguanine; mercaptopurine; methotrexate; platinum coordination complexes such as cisplatin, oxaliplatin and carboplatin; vinblastine; platinum; etoposide (VP-16); ifosfamide; mitoxantrone; vincristine; vinorelbine; novantrone; teniposide; edatrexate; daunomycin; aminopterin; xeloda; ibandronate; irinotecan (e.g., CPT-11); topoisomerase inhibitor RFS 2000; difluorometlhylornithine (DMFO); retinoids such as retinoic acid; capecitabine; cisplatin (CDDP), carboplatin, procarbazine, mechlorethamine, cyclophosphamide, camptothecin, ifosfamide, melphalan, chlorambucil, busulfan, nitrosurea, dactinomycin, daunorubicin, doxorubicin, bleomycin, plicomycin, mitomycin, etoposide (VP16), tamoxifen, raloxifene, estrogen receptor binding agents, taxol, paclitaxel, docetaxel, gemcitabien, navelbine, farnesyl-protein tansferase inhibitors, transplatinum, 5-fluorouracil, vincristin, vinblastin and methotrexate and pharmaceutically acceptable salts, acids or derivatives of any of the above. In some embodiments, the chemotherapeutic agent is a chemotherapeutic drug which inhibits one or more kinases which is misregulated or overexpressed in a cancer. In some embodiments, the chemotherapeutic drug is afatinib, aflibercept, axitinib, bevacizumab, bosutinib, cabozantinib, cetuximab, crizotinib, dasatinib, erlotinib, forstamatinib, gefitinib, ibrutinib, imatinib, lapatinib, lenvatinib, mubritinib, nilotinib, panitumumab, pazopanib, pegaptanib, ponatinib, ranibizumab, regorafenib, ruxolitinib, sorafenib, sunitinib, SU6656, trastuzumab, tofacitinib, vandetanib, or vemurafenib.

V. Definitions

When used in the context of a chemical group: "hydrogen" means —H; "hydroxy" means —OH; "oxo" means =O; "carbonyl" means —C(=O)—; "carboxy" means —C(=O)OH (also written as —COOH or —CO₂H); "halo" means independently —F, —Cl, —Br or —I; "amino" means —NH₂; "hydroxyamino" means —NHOH; "nitro" means —NO₂; imino means =NH; "cyano" means —CN; "isocyanate" means —N=C=O; "azido" means —N₃; in a monovalent context "phosphate" means —OP(O)(OH)₂ or a deprotonated form thereof in a divalent context "phosphate" means —OP(O)(OH)O— or a deprotonated form thereof; "mercapto" means —SH; and "thio" means =S; "sulfonyl" means —S(O)₂—; "hydroxysulfonyl" means —S(O)₂OH; "sulfonamide" means —S(O)₂NH₂; and "sulfinyl" means —S(O)—.

In the context of chemical formulas, the symbol "—" means a single bond, "=" means a double bond, and "≡" means triple bond. The symbol "----" represents an optional bond, which if present is either single or double. The symbol "═══" represents a single bond or a double bond. Thus, for example, the formula

includes

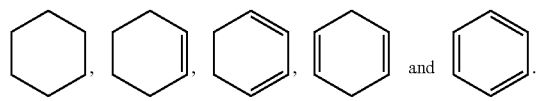

And it is understood that no one such ring atom forms part of more than one double bond. Furthermore, it is noted that the covalent bond symbol "—", when connecting one or two stereogenic atoms, does not indicate any preferred stereochemistry. Instead, it covers all stereoisomers as well as mixtures thereof. The symbol "∿∿", when drawn perpendicularly across a bond (e.g.,

for methyl) indicates a point of attachment of the group. It is noted that the point of attachment is typically only identified in this manner for larger groups in order to assist the reader in unambiguously identifying a point of attachment. The symbol "◄━" means a single bond where the group attached to the thick end of the wedge is "out of the page." The symbol "▮▮▮▮" means a single bond where the group attached to the thick end of the wedge is "into the page". The symbol "∿∿" means a single bond where the geometry around a double bond (e.g., either E or Z) is undefined. Both options, as well as combinations thereof are therefore intended. Any undefined valency on an atom of a structure shown in this application implicitly represents a hydrogen atom bonded to that atom. A bold dot on a carbon atom indicates that the hydrogen attached to that carbon is oriented out of the plane of the paper.

When a group "R" is depicted as a "floating group" on a ring system, for example, in the formula:

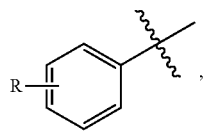

then R may replace any hydrogen atom attached to any of the ring atoms, including a depicted, implied, or expressly defined hydrogen, so long as a stable structure is formed. When a group "R" is depicted as a "floating group" on a fused ring system, as for example in the formula:

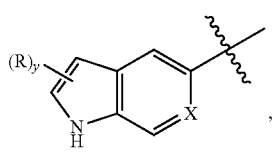

then R may replace any hydrogen attached to any of the ring atoms of either of the fused rings unless specified otherwise. Replaceable hydrogens include depicted hydrogens (e.g., the hydrogen attached to the nitrogen in the formula above), implied hydrogens (e.g., a hydrogen of the formula above that is not shown but understood to be present), expressly defined hydrogens, and optional hydrogens whose presence depends on the identity of a ring atom (e.g., a hydrogen attached to group X, when X equals —CH—), so long as a stable structure is formed. In the example depicted, R may reside on either the 5-membered or the 6-membered ring of the fused ring system. In the formula above, the subscript letter "y" immediately following the group "R" enclosed in parentheses, represents a numeric variable. Unless specified otherwise, this variable can be 0, 1, 2, or any integer greater than 2, only limited by the maximum number of replaceable hydrogen atoms of the ring or ring system.

For the chemical groups and compound classes, the number of carbon atoms in the group or class is as indicated as follows: "Cn" defines the exact number (n) of carbon atoms in the group/class. "C≤n" defines the maximum number (n) of carbon atoms that can be in the group/class, with the minimum number as small as possible for the group/class in question, e.g., it is understood that the minimum number of carbon atoms in the group "alkenyl$_{(C≤8)}$" or the class "alkene$_{(C≤8)}$" is two. Compare with "alkoxy$_{(C≤10)}$", which designates alkoxy groups having from 1 to 10 carbon atoms. "Cn-n'" defines both the minimum (n) and maximum number (n') of carbon atoms in the group. Thus, "alkyl$_{(C2-10)}$" designates those alkyl groups having from 2 to 10 carbon atoms. These carbon number indicators may precede or follow the chemical groups or class it modifies and it may or may not be enclosed in parenthesis, without signifying any change in meaning. Thus, the terms "C5 olefin", "C5-olefin", "olefin$_{(C5)}$", and "olefin$_{C5}$" are all synonymous.

The term "saturated" when used to modify a compound or chemical group means the compound or chemical group has no carbon-carbon double bonds and no carbon-carbon triple bonds, except as noted below. When the term is used to modify an atom, it means that the atom is not part of any double or triple bond. In the case of substituted versions of saturated groups, one or more carbon oxygen double bond or a carbon nitrogen double bond may be present. And when such a bond is present, then carbon-carbon double bonds that may occur as part of keto-enol tautomerism or imine/enamine tautomerism are not precluded. When the term "saturated" is used to modify a solution of a substance, it means that no more of that substance can dissolve in that solution.

The term "aliphatic" when used without the "substituted" modifier signifies that the compound or chemical group so modified is an acyclic or cyclic, but non-aromatic hydrocarbon compound or group. In aliphatic compounds/groups, the carbon atoms can be joined together in straight chains, branched chains, or non-aromatic rings (alicyclic). Aliphatic compounds/groups can be saturated, that is joined by single carbon-carbon bonds (alkanes/alkyl), or unsaturated, with one or more carbon-carbon double bonds (alkenes/alkenyl) or with one or more carbon-carbon triple bonds (alkynes/alkynyl).

The term "aromatic" when used to modify a compound or a chemical group atom means the compound or chemical group contains a planar unsaturated ring of atoms that is stabilized by an interaction of the bonds forming the ring.

The term "alkyl" when used without the "substituted" modifier refers to a monovalent saturated aliphatic group with a carbon atom as the point of attachment, a linear or branched acyclic structure, and no atoms other than carbon and hydrogen. The groups —CH$_3$ (Me), —CH$_2$CH$_3$ (Et), —CH$_2$CH$_2$CH$_3$ (n-Pr or propyl), —CH(CH$_3$)$_2$ (i-Pr, $^i$Pr or isopropyl), —CH$_2$CH$_2$CH$_2$CH$_3$ (n-Bu), —CH(CH$_3$)CH$_2$CH$_3$ (sec-butyl), —CH$_2$CH(CH$_3$)$_2$ (isobutyl), —C(CH$_3$)$_3$ (tert-butyl, t-butyl, t-Bu or $^t$Bu), and —CH$_2$C(CH$_3$)$_3$ (neo-pentyl) are non-limiting examples of alkyl groups. The term "alkanediyl" when used without the "substituted" modifier refers to a divalent saturated aliphatic group, with one or two saturated carbon atom(s) as the point(s) of attachment, a linear or branched acyclic structure, no carbon-carbon double or triple bonds, and no atoms other than carbon and hydrogen. The groups —CH$_2$—(methylene), —CH$_2$CH$_2$—, —CH$_2$C(CH$_3$)$_2$CH$_2$—, and —CH$_2$CH$_2$CH$_2$— are non-limiting examples of alkanediyl groups. The term "alkylidene" when used without the "substituted" modifier refers to the divalent group =CRR' in which R and R' are independently hydrogen or alkyl. Non-limiting examples of alkylidene groups include: =CH$_2$, =CH(CH$_2$CH$_3$), and =C(CH$_3$)$_2$. An "alkane" refers to the class of compounds having the formula H—R, wherein R is alkyl as this term is defined above. When any of these terms is used with the "substituted" modifier one or more hydrogen atom has been independently replaced by —OH, —F, —Cl, —Br, —I, NH$_2$, —NO$_2$, —CO$_2$H, —CO$_2$CH$_3$, —CN, —SH, —OCH$_3$, —OCH$_2$CH$_3$, —C(O)CH$_3$, —NHCH$_3$, —NHCH$_2$CH$_3$, —N(CH$_3$)$_2$, —C(O)NH$_2$, —C(O)NHCH$_3$, —C(O)N(CH$_3$)$_2$, —OC(O)CH$_3$, —NHC(O)CH$_3$, —S(O)$_2$OH, or —S(O)$_2$NH$_2$. The following groups are non-limiting examples of substituted alkyl groups: —CH$_2$OH, —CH$_2$Cl, —CF$_3$, —CH$_2$CN, —CH$_2$C(O)OH, —CH$_2$C(O)OCH$_3$, —CH$_2$C(O)NH$_2$, —CH$_2$C(O)CH$_3$, —CH$_2$OCH$_3$, —CH$_2$OC(O)CH$_3$, —CH$_2$NH$_2$, —CH$_2$N(CH$_3$)$_2$, and —CH$_2$CH$_2$Cl. The term "haloalkyl" is a subset of substituted alkyl, in which the hydrogen atom replacement is limited to halo (i.e. —F, —Cl, —Br, or —I) such that no other atoms aside from carbon, hydrogen and halogen are present. The group, —CH$_2$Cl is a non-limiting example of a haloalkyl. The term "fluoroalkyl" is a subset of substituted alkyl, in which the hydrogen atom replacement is limited to fluoro such that no other atoms aside from carbon, hydrogen and fluorine are present. The groups —CH$_2$F, —CF$_3$, and —CH$_2$CF$_3$ are non-limiting examples of fluoroalkyl groups.

The term "aryl" when used without the "substituted" modifier refers to a monovalent unsaturated aromatic group with an aromatic carbon atom as the point of attachment, said carbon atom forming part of a one or more six-membered aromatic ring structure, wherein the ring atoms are all carbon, and wherein the group consists of no atoms other than carbon and hydrogen. If more than one ring is present, the rings may be fused or unfused. As used herein, the term does not preclude the presence of one or more alkyl or aralkyl groups (carbon number limitation permitting) attached to the first aromatic ring or any additional aromatic ring present. Non-limiting examples of aryl groups include phenyl (Ph), methylphenyl, (dimethyl)phenyl, —$C_6H_4CH_2CH_3$ (ethylphenyl), naphthyl, and a monovalent group derived from biphenyl. The term "arenediyl" when used without the "substituted" modifier refers to a divalent aromatic group with two aromatic carbon atoms as points of attachment, said carbon atoms forming part of one or more six-membered aromatic ring structure(s) wherein the ring atoms are all carbon, and wherein the monovalent group consists of no atoms other than carbon and hydrogen. As used herein, the term does not preclude the presence of one or more alkyl, aryl or aralkyl groups (carbon number limitation permitting) attached to the first aromatic ring or any additional aromatic ring present. If more than one ring is present, the rings may be fused or unfused. Unfused rings may be connected via one or more of the following: a covalent bond, alkanediyl, or alkenediyl groups (carbon number limitation permitting). Non-limiting examples of arenediyl groups include:

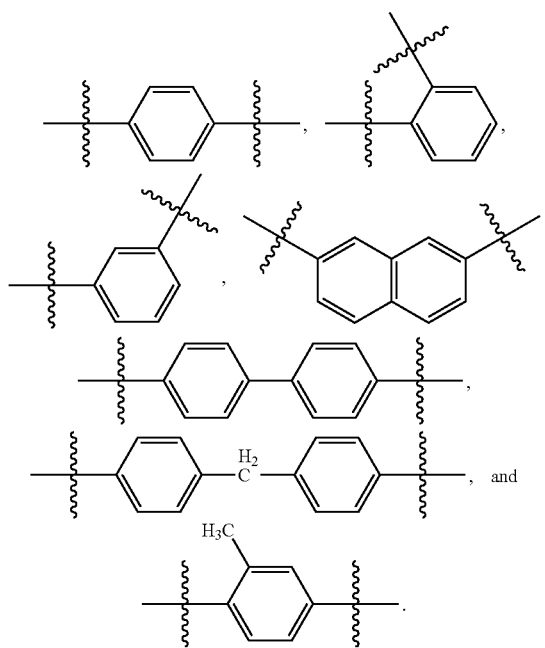

An "arene" refers to the class of compounds having the formula H—R, wherein R is aryl as that term is defined above. Benzene and toluene are non-limiting examples of arenes. When any of these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —C(O)$NHCH_3$, —C(O)$N(CH_3)_2$, —OC(O)$CH_3$, —NHC(O)$CH_3$, —S(O)$_2$OH, or —S(O)$_2$$NH_2$.

The term "heteroaryl" when used without the "substituted" modifier refers to a monovalent aromatic group with an aromatic carbon atom or nitrogen atom as the point of attachment, said carbon atom or nitrogen atom forming part of one or more aromatic ring structures wherein at least one of the ring atoms is nitrogen, oxygen or sulfur, and wherein the heteroaryl group consists of no atoms other than carbon, hydrogen, aromatic nitrogen, aromatic oxygen and aromatic sulfur. If more than one ring is present, the rings may be fused or unfused. As used herein, the term does not preclude the presence of one or more alkyl, aryl, and/or aralkyl groups (carbon number limitation permitting) attached to the aromatic ring or aromatic ring system. Non-limiting examples of heteroaryl groups include furanyl, imidazolyl, indolyl, indazolyl (Im), isoxazolyl, methylpyridinyl, oxazolyl, phenylpyridinyl, pyridinyl (pyridyl), pyrrolyl, pyrimidinyl, pyrazinyl, quinolyl, quinazolyl, quinoxalinyl, triazinyl, tetrazolyl, thiazolyl, thienyl, and triazolyl. The term "N-heteroaryl" refers to a heteroaryl group with a nitrogen atom as the point of attachment. The term "heteroarenediyl" when used without the "substituted" modifier refers to an divalent aromatic group, with two aromatic carbon atoms, two aromatic nitrogen atoms, or one aromatic carbon atom and one aromatic nitrogen atom as the two points of attachment, said atoms forming part of one or more aromatic ring structure(s) wherein at least one of the ring atoms is nitrogen, oxygen or sulfur, and wherein the divalent group consists of no atoms other than carbon, hydrogen, aromatic nitrogen, aromatic oxygen and aromatic sulfur. If more than one ring is present, the rings may be fused or unfused. Unfused rings may be connected via one or more of the following: a covalent bond, alkanediyl, or alkenediyl groups (carbon number limitation permitting). As used herein, the term does not preclude the presence of one or more alkyl, aryl, and/or aralkyl groups (carbon number limitation permitting) attached to the aromatic ring or aromatic ring system. Non-limiting examples of heteroarenediyl groups include:

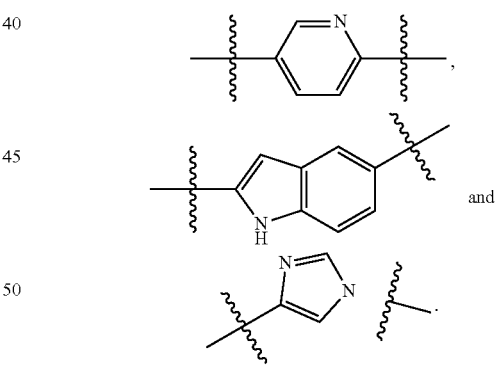

A "heteroarene" refers to the class of compounds having the formula H—R, wherein R is heteroaryl. Pyridine and quinoline are non-limiting examples of heteroarenes. When these terms are used with the "substituted" modifier one or more hydrogen atom has been independently replaced by —OH, —F, —Cl, —Br, —I, —$NH_2$, —$NO_2$, —$CO_2H$, —$CO_2CH_3$, —CN, —SH, —$OCH_3$, —$OCH_2CH_3$, —C(O)$CH_3$, —$NHCH_3$, —$NHCH_2CH_3$, —$N(CH_3)_2$, —C(O)$NH_2$, —C(O)$NHCH_3$, —C(O)$N(CH_3)_2$, —OC(O)$CH_3$, —NHC(O)$CH_3$, —S(O)$_2$OH, or —S(O)$_2$$NH_2$.

The term "acyl" when used without the "substituted" modifier refers to the group —C(O)R, in which R is a hydrogen, alkyl, cycloalkyl, alkenyl, aryl, aralkyl or heteroaryl, as those terms are defined above. The groups, —CHO, —C(O)CH₃ (acetyl, Ac), —C(O)CH₂CH₃, —C(O)CH₂CH₂CH₃, —C(O)CH(CH₃)₂, —C(O)CH(CH₂)₂, —C(O)C₆H₅, —C(O)C₆H₄CH₃, —C(O)CH₂C₆H₅, —C(O)(imidazolyl) are non-limiting examples of acyl groups. A "thioacyl" is defined in an analogous manner, except that the oxygen atom of the group —C(O)R has been replaced with a sulfur atom, —C(S)R. The term "aldehyde" corresponds to an alkane, as defined above, wherein at least one of the hydrogen atoms has been replaced with a —CHO group. The term "ester" refers to the group —C(O)R, in which R is an alkoxy. When any of these terms are used with the "substituted" modifier one or more hydrogen atom (including a hydrogen atom directly attached to the carbon atom of the carbonyl or thiocarbonyl group, if any) has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups, —C(O)CH₂CF₃, —CO₂H (carboxyl), —CO₂CH₃ (methylcarboxyl), —CO₂CH₂CH₃, —C(O)NH₂ (carbamoyl), and —CON(CH₃)₂, are non-limiting examples of substituted acyl groups.

The term "alkoxy" when used without the "substituted" modifier refers to the group —OR, in which R is an alkyl, as that term is defined above. Non-limiting examples include: —OCH₃ (methoxy), —OCH₂CH₃ (ethoxy), —OCH₂CH₂CH₃, —OCH(CH₃)₂ (isopropoxy), —OC(CH₃)₃ (tert-butoxy), —OCH(CH₂)₂, —O-cyclopentyl, and —O-cyclohexyl. The terms "cycloalkoxy", "alkenyloxy", "alkynyloxy", "aryloxy", "aralkoxy", "heteroaryloxy", "heterocycloalkoxy", and "acyloxy", when used without the "substituted" modifier, refers to groups, defined as —OR, in which R is cycloalkyl, alkenyl, alkynyl, aryl, aralkyl, heteroaryl, heterocycloalkyl, and acyl, respectively. The term "alkylthio" and "acylthio" when used without the "substituted" modifier refers to the group —SR, in which R is an alkyl and acyl, respectively. The term "alcohol" corresponds to an alkane, as defined above, wherein at least one of the hydrogen atoms has been replaced with a hydroxy group. The term "ether" corresponds to an alkane, as defined above, wherein at least one of the hydrogen atoms has been replaced with an alkoxy group. When any of these terms is used with the "substituted" modifier one or more hydrogen atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂.

The term "alkylamino" when used without the "substituted" modifier refers to the group —NHR, in which R is an alkyl, as that term is defined above. Non-limiting examples include: —NHCH₃ and —NHCH₂CH₃. The term "dialkylamino" when used without the "substituted" modifier refers to the group —NRR', in which R and R' can be the same or different alkyl groups, or R and R' can be taken together to represent an alkanediyl. Non-limiting examples of dialkylamino groups include: —N(CH₃)₂ and —N(CH₃)(CH₂CH₃). The terms "cycloalkylamino", "alkenylamino", "alkynylamino", "arylamino", "aralkylamino", "heteroarylamino", "heterocycloalkylamino", "alkoxyamino", and "alkylsulfonylamino" when used without the "substituted" modifier, refers to groups, defined as —NHR, in which R is cycloalkyl, alkenyl, alkynyl, aryl, aralkyl, heteroaryl, heterocycloalkyl, alkoxy, and alkylsulfonyl, respectively. A non-limiting example of an arylamino group is —NHC₆H₅. The term "amido" (acylamino), when used without the "substituted" modifier, refers to the group —NHR, in which R is acyl, as that term is defined above. A non-limiting example of an amido group is —NHC(O)CH₃. The term "alkylimino" when used without the "substituted" modifier refers to the divalent group =NR, in which R is an alkyl, as that term is defined above. When any of these terms is used with the "substituted" modifier one or more hydrogen atom attached to a carbon atom has been independently replaced by —OH, —F, —Cl, —Br, —I, —NH₂, —NO₂, —CO₂H, —CO₂CH₃, —CN, —SH, —OCH₃, —OCH₂CH₃, —C(O)CH₃, —NHCH₃, —NHCH₂CH₃, —N(CH₃)₂, —C(O)NH₂, —C(O)NHCH₃, —C(O)N(CH₃)₂, —OC(O)CH₃, —NHC(O)CH₃, —S(O)₂OH, or —S(O)₂NH₂. The groups —NHC(O)OCH₃ and —NHC(O)NHCH₃ are non-limiting examples of substituted amido groups.

The use of the word "a" or "an," when used in conjunction with the term "comprising" in the claims and/or the specification may mean "one," but it is also consistent with the meaning of "one or more," "at least one," and "one or more than one."

Throughout this application, the term "about" is used to indicate that a value includes the inherent variation of error for the device, the method being employed to determine the value, or the variation that exists among the study subjects.

The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps.

The term "effective," as that term is used in the specification and/or claims, means adequate to accomplish a desired, expected, or intended result. "Effective amount," "Therapeutically effective amount" or "pharmaceutically effective amount" when used in the context of treating a patient or subject with a compound means that amount of the compound which, when administered to a subject or patient for treating a disease, is sufficient to effect such treatment for the disease.

As used herein, the term "IC₅₀" refers to an inhibitory dose which is 50% of the maximum response obtained. This quantitative measure indicates how much of a particular drug or other substance (inhibitor) is needed to inhibit a given biological, biochemical or chemical process (or component of a process, i.e. an enzyme, cell, cell receptor or microorganism) by half.

An "isomer" of a first compound is a separate compound in which each molecule contains the same constituent atoms as the first compound, but where the configuration of those atoms in three dimensions differs.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

As used herein, the term "patient" or "subject" refers to a living mammalian organism, such as a human, monkey, horse, cow, sheep, goat, dog, cat, mouse, rat, guinea pig, or transgenic species thereof. In certain embodiments, the patient or subject is a primate. Non-limiting examples of human subjects are adults, juveniles, infants and fetuses.

As generally used herein "pharmaceutically acceptable" refers to those compounds, materials, compositions, and/or dosage forms which are, within the scope of sound medical judgment, suitable for use in contact with the tissues, organs, and/or bodily fluids of human beings and animals without excessive toxicity, irritation, allergic response, or other problems or complications commensurate with a reasonable benefit/risk ratio.

"Pharmaceutically acceptable salts" means salts of compounds of the present invention which are pharmaceutically acceptable, as defined above, and which possess the desired pharmacological activity. Such salts include acid addition salts formed with inorganic acids such as hydrochloric acid, hydrobromic acid, sulfuric acid, nitric acid, phosphoric acid, and the like; or with organic acids such as 1,2-ethanedisulfonic acid, 2-hydroxyethanesulfonic acid, 2-naphthalenesulfonic acid, 3-phenylpropionic acid, 4,4'-methylenebis(3-hydroxy-2-ene-1-carboxylic acid), 4-methylbicyclo[2.2.2]oct-2-ene-1-carboxylic acid, acetic acid, aliphatic mono- and dicarboxylic acids, aliphatic sulfuric acids, aromatic sulfuric acids, benzenesulfonic acid, benzoic acid, camphorsulfonic acid, carbonic acid, cinnamic acid, citric acid, cyclopentanepropionic acid, ethanesulfonic acid, fumaric acid, glucoheptonic acid, gluconic acid, glutamic acid, glycolic acid, heptanoic acid, hexanoic acid, hydroxynaphthoic acid, lactic acid, laurylsulfuric acid, maleic acid, malic acid, malonic acid, mandelic acid, methanesulfonic acid, muconic acid, o-(4-hydroxybenzoyl)benzoic acid, oxalic acid, p-chlorobenzenesulfonic acid, phenyl-substituted alkanoic acids, propionic acid, p-toluenesulfonic acid, pyruvic acid, salicylic acid, stearic acid, succinic acid, tartaric acid, tertiarybutylacetic acid, trimethylacetic acid, and the like. Pharmaceutically acceptable salts also include base addition salts which may be formed when acidic protons present are capable of reacting with inorganic or organic bases. Acceptable inorganic bases include sodium hydroxide, sodium carbonate, potassium hydroxide, aluminum hydroxide and calcium hydroxide. Acceptable organic bases include ethanolamine, diethanolamine, triethanolamine, tromethamine, N-methylglucamine and the like. It should be recognized that the particular anion or cation forming a part of any salt of this invention is not critical, so long as the salt, as a whole, is pharmacologically acceptable. Additional examples of pharmaceutically acceptable salts and their methods of preparation and use are presented in *Handbook of Pharmaceutical Salts: Properties, and Use* (P. H. Stahl & C. G. Wermuth eds., Verlag Helvetica Chimica Acta, 2002).

The term "pharmaceutically acceptable carrier," as used herein means a pharmaceutically-acceptable material, composition or vehicle, such as a liquid or solid filler, diluent, excipient, solvent or encapsulating material, involved in carrying or transporting a chemical agent.

"Prevention" or "preventing" includes: (1) inhibiting the onset of a disease in a subject or patient which may be at risk and/or predisposed to the disease but does not yet experience or display any or all of the pathology or symptomatology of the disease, and/or (2) slowing the onset of the pathology or symptomatology of a disease in a subject or patient which may be at risk and/or predisposed to the disease but does not yet experience or display any or all of the pathology or symptomatology of the disease.

A "stereoisomer" or "optical isomer" is an isomer of a given compound in which the same atoms are bonded to the same other atoms, but where the configuration of those atoms in three dimensions differs. "Enantiomers" are stereoisomers of a given compound that are mirror images of each other, like left and right hands. "Diastereomers" are stereoisomers of a given compound that are not enantiomers. Chiral molecules contain a chiral center, also referred to as a stereocenter or stereogenic center, which is any point, though not necessarily an atom, in a molecule bearing groups such that an interchanging of any two groups leads to a stereoisomer. In organic compounds, the chiral center is typically a carbon, phosphorus or sulfur atom, though it is also possible for other atoms to be stereocenters in organic and inorganic compounds. A molecule can have multiple stereocenters, giving it many stereoisomers. In compounds whose stereoisomerism is due to tetrahedral stereogenic centers (e.g., tetrahedral carbon), the total number of hypothetically possible stereoisomers will not exceed $2^n$, where n is the number of tetrahedral stereocenters. Molecules with symmetry frequently have fewer than the maximum possible number of stereoisomers. A 50:50 mixture of enantiomers is referred to as a racemic mixture. Alternatively, a mixture of enantiomers can be enantiomerically enriched so that one enantiomer is present in an amount greater than 50%. Typically, enantiomers and/or diastereomers can be resolved or separated using techniques known in the art. It is contemplated that that for any stereocenter or axis of chirality for which stereochemistry has not been defined, that stereocenter or axis of chirality can be present in its R form, S form, or as a mixture of the R and S forms, including racemic and non-racemic mixtures. As used herein, the phrase "substantially free from other stereoisomers" means that the composition contains ≤15%, more preferably ≤10%, even more preferably ≤5%, or most preferably ≤1% of another stereoisomer(s).

"Treatment" or "treating" includes (1) inhibiting a disease in a subject or patient experiencing or displaying the pathology or symptomatology of the disease (e.g., arresting further development of the pathology and/or symptomatology), (2) ameliorating a disease in a subject or patient that is experiencing or displaying the pathology or symptomatology of the disease (e.g., reversing the pathology and/or symptomatology), and/or (3) effecting any measurable decrease in a disease in a subject or patient that is experiencing or displaying the pathology or symptomatology of the disease.

The above definitions supersede any conflicting definition in any reference that is incorporated by reference herein. The fact that certain terms are defined, however, should not be considered as indicative that any term that is undefined is indefinite. Rather, all terms used are believed to describe the invention in terms such that one of ordinary skill can appreciate the scope and practice the present invention.

VI. Examples

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

Modular Design of DNA Binding Agents

The inventors used a "modular" approach to the design of unique DNA binding agents. The "modular" design strategy combines intercalation and groove-binding modes into molecules with the requisite chirality and binding-site size to impart meaningful selectivity. They utilized a building block library of anthracycline scaffolds and distamycin-based fragments that allow for modular design to consider small molecule binders targeting extended GC and AT containing sequences. The inventors show that connecting distamycin pyrrole-containing fragments with the anthracycline module has very specific requirements. The use of an aromatic linker resulted in the synthesis of compounds listed in the Table 1 (below).

TABLE 1

Structures of synthesized compounds.

| Structure | Compound |
|---|---|
| 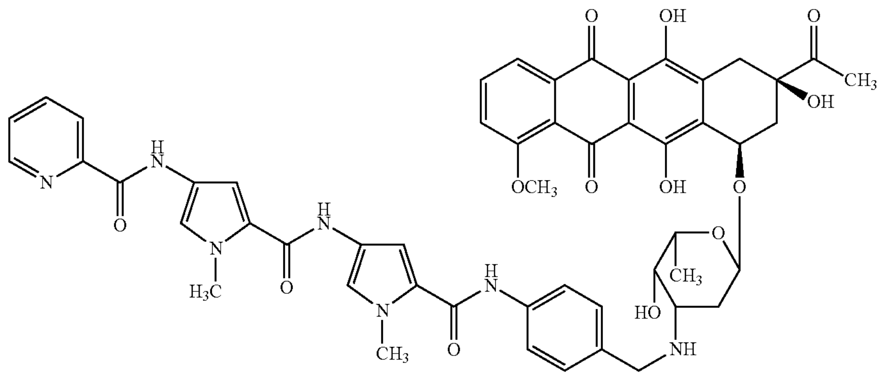 | WP1244 |
| 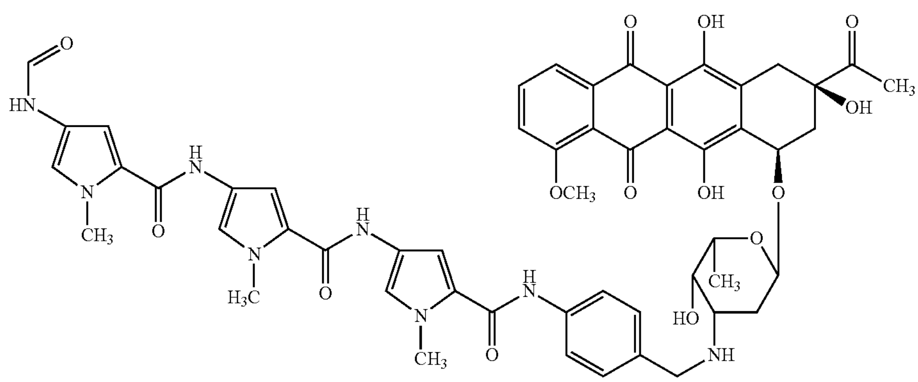 | WP1249 |
| 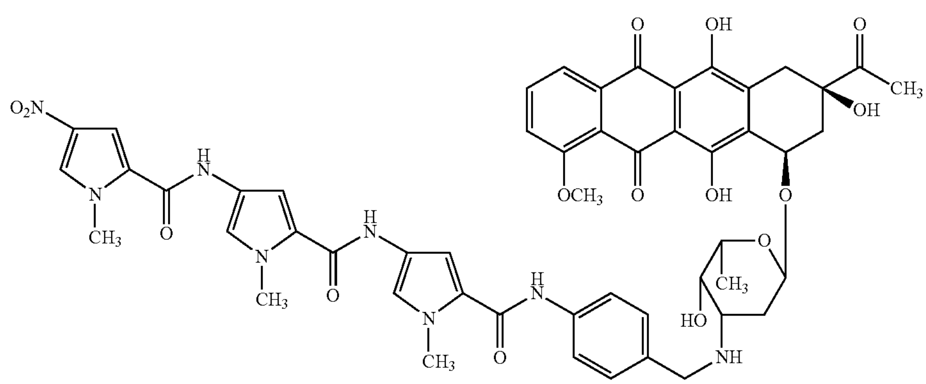 | WP1276 |

TABLE 1-continued

Structures of synthesized compounds.

| Structure | Compound |
|---|---|
| 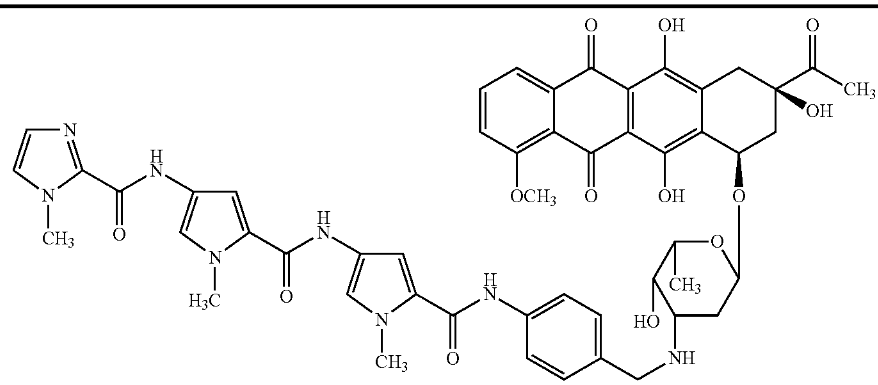 | WP1248 |
| 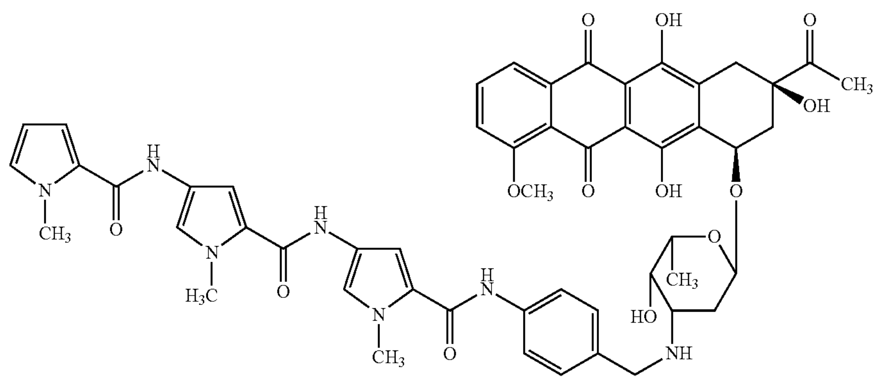 | WP1243 |
| 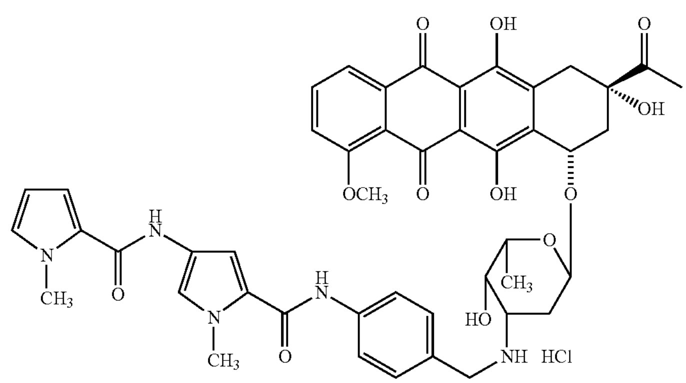 | WP1402 |
| 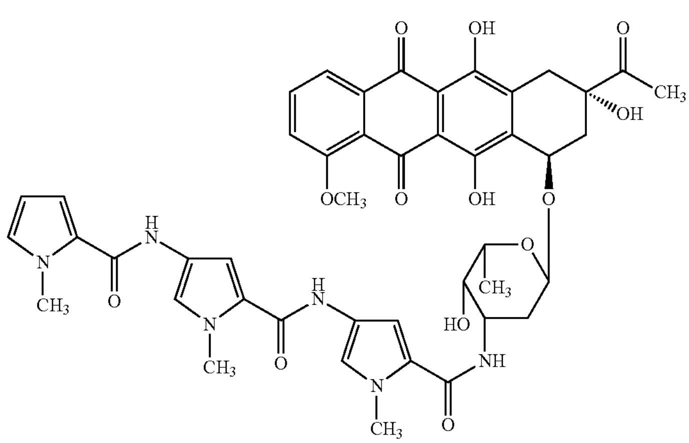 | WP1277 |

TABLE 1-continued

Structures of synthesized compounds.

| Structure | Compound |
|---|---|
| 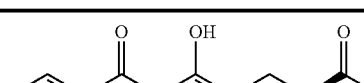 | WP1401 |

Example 2

Pharmacokinetic Evaluation of WP1244

In particular, compound WP1244 (see FIGS. 1A-B) was found to be exceedingly potent having in vitro $IC_{50}$ values in the subnanomolar range and is currently being studied for its therapeutic potential in preclinical studies. WP1244 has a relatively high molecular weight (MW) (981.3) having a polyamide moiety attached to the amino sugar. A previous 5-mice pilot study performed with WP1244 confirmed the presence of WP1244 in murine brain tissue, and mean normalized concentrations in the plasma and brain were 283+/−128 ng/mL (range 159-487 ng/mL) and 122+/−67.6 ng/g (range 43-203 ng/g), respectively, one hour following a single ~5 mg/kg intravenous dose. This pilot single-dose pharmacokinetic study was followed by a complete single-dose pharmacokinetic/biodistribution study which was designed to better elucidate the plasma time-course and tissue biodistribution, particularly in brain tissue, of WP1244. This study involve the use of 55 animals and a dose of 10 mg/kg. The experiment was conducted over a 24 h interval and the methods and results are outlined below.

Mouse Plasma PK and Brain Distribution Study following Single IV Dose—WP1244 was administered intravenously by rapid IV push to 55 male CD1 mice (Charles River Lab, Wilmington, Mass.) at a dose of 10 mg/kg. Each mouse (mean weight 22.0 g, range 20.7-26.6 g) was given a volume of 0.1 mL of a 2.2 mg/mL WP1244 solution formulated in DMSO:water (50:50, v/v). Five animals were assigned to one of 11 groups segregated by time, spanning the length of the 24-hour study period. One cohort of animals was sacrificed at each of the following time points and mouse plasma and tissues of interest, were harvested for analysis. The time points were as follows: 5, 15, 30, 45 minutes, 1, 2, 4, 6, 8, 12, and 24 hours following administration by intravenous bolus. Samples (plasma and tissues) were frozen and stored at −80° C. until subsequent analysis by LC/MS/MS.

Sample preparation and drug isolation (extraction) from plasma utilized the same fundamental approach used in pharmacokinetic and biodistribution studies of other anthracyclines previously conducted by the inventors. Briefly, WP1244 was extracted from a volume (0.1 mL) of mouse plasma using a solid-phase extraction method. Liquid-liquid extraction by a chloroform: 2-propanol (80:20, v/v) mixture was utilized to isolate the analyte from mouse brain tissue. An 8-point plasma extracted calibration curve was created to span a dynamic concentration range of WP1244 of 1-1000 ng/mL (1, 2.5, 10, 25, 50, 100, 500, and 1000 ng/mL) for the quantitative measurement of WP1244 extracted from mouse plasma, while a brain tissue derived calibration curve was utilized for determination of brain tissue concentrations of drug over a range of 10-1000 ng/g tissue. Samples exceeding the dynamic range of the calibration curve were re-analyzed following dilution in extraction buffers.

Quantitative sample analysis was performed by chromatographic separation and identification/quantification using mass spectrometry (LC/MS/MS); the specific instrumentation used was an Agilent HP1100 Series liquid chromatograph in tandem with a Micromass Quattro Micro (Micro2) mass spectrometer. A Phenomenex® Luna C5, 4.6×50 mm, 3.5 µm) analytical column was used for chromatographic separation and peak resolution. As mentioned before, sample analysis utilized the same fundamental validated methods developed previously for the quantitative analysis of other anthracyclines studied by the inventors.

Results—WP1244 was present in all plasma and brain tissue samples, except the pre-dose samples, spanning the 24 hour time course of this single-dose, IV drug study (FIG. 2). The results of the plasma sample analysis revealed that similar to other agents in this drug class, the pharmacokinetics of WP1244 was best fit using a standard 2-compartment model in this murine model. Drug clearance was 41 ml/h/kg, and volumes of distribution parameters were 9.7, 326, and 336 mL/kg for $V_c$, $V_p$, and $V_{ss}$, respectively. Mean peak plasma concentration was determined to be 3.7 mg/mL, five minutes after drug administration, and the mean nadir concentration of WP1244 24 hours after IV bolus injection was 21.5 ng/mL. The area-under-the-curve for WP1244 was 250 mg/mL*hr.

WP1244 concentrations in brain tissue exceed the simultaneously measured plasma concentrations (with the exception of the 5 min timepoint) almost by an order of magnitude over the entire measured interval, indicating that drug distribution was rapid and that the drug was sequestered in brain tissue (as demonstrated by the brain tissue to plasma concentration ratio always exceeding 1). The mean peak concentration of WP1244 in brain tissue was 915 ng/g tissue and occurred at 15 minutes post dose, the nadir brain tissue concentration at 24 hours exceeded 100 ng/g tissue. Measured concentrations in plasma and brain tissue were in excess of the subnanomolar concentrations associated with cytotoxic activity in in vitro studies throughout the 24 hours experimental period. As a confirmation the values reported here are nearly identical to those observed in the previous pilot feasibility PK study.

Figure 3:
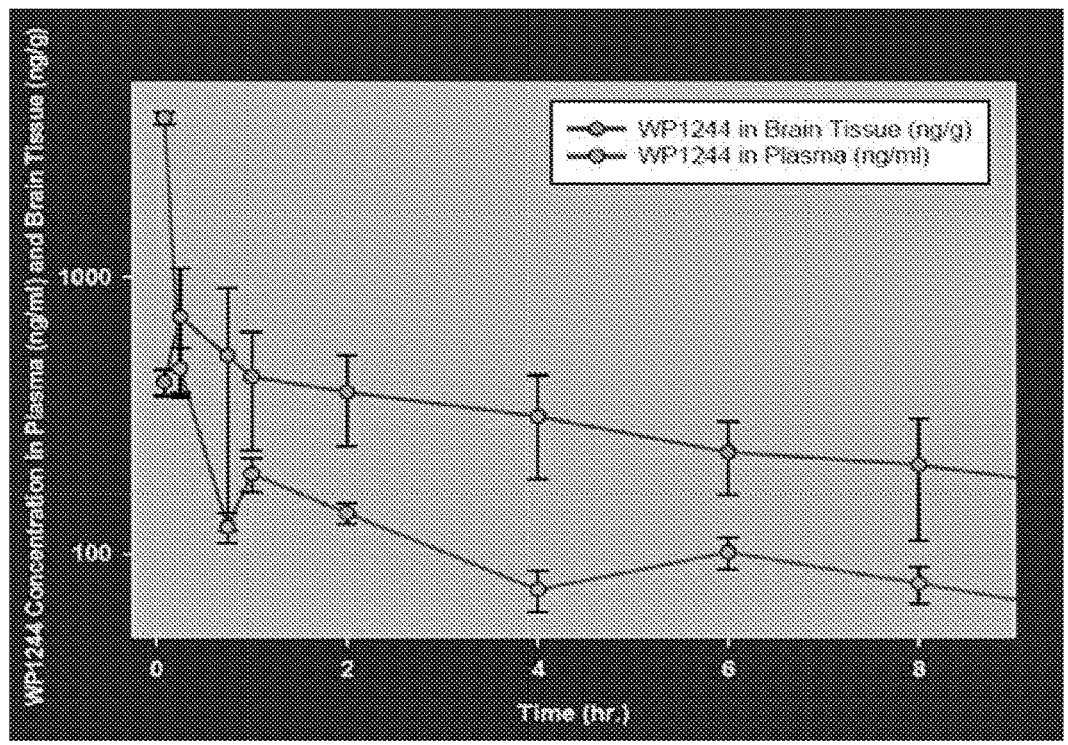
FIG. 3—WP1244 Mouse Plasma Pharmacokinetics and Brain Tissue Biodistribution after 10 mg/kg IV dose (0-8 hr).
Figure 4:
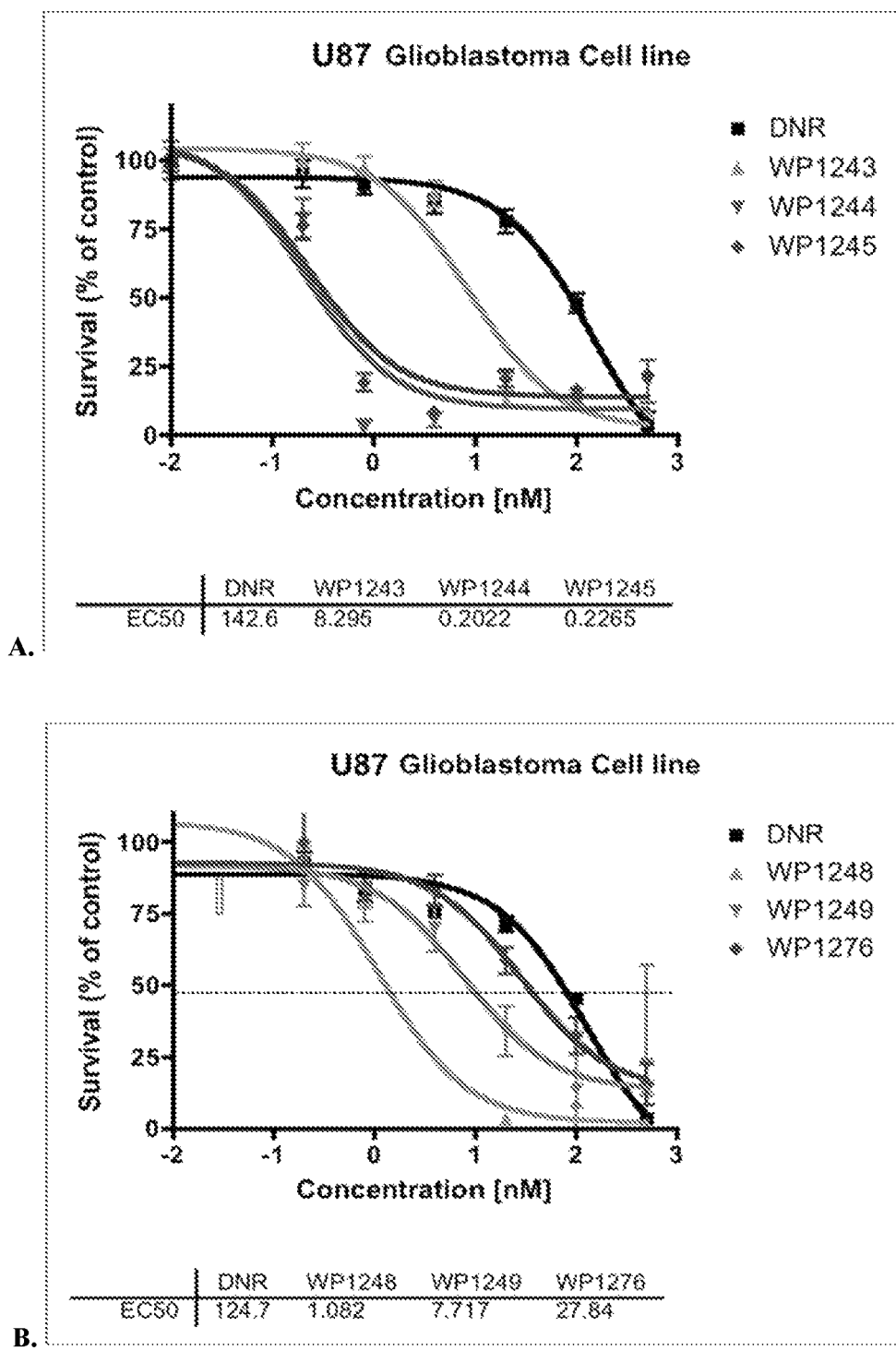
FIGS. 4A-B—In vitro evaluation of WP1244 and its analogs. In vitro evaluation of WP1244 and its analogs.

FIG. 3 shows an expanded view of the plasma and tissue WP1244 drug concentration versus time profile for the 0 to 8 hour interval showing the 3-4 fold higher concentration of WP1244 in brain tissue over that interval. The intravenous bolus administration of WP1244 at a dose of 10 mg/kg to mice produced no acute clinically observable toxicity in the study animals for up to 24 hours following drug dosing. FIGS. 4A-B and Table 2 (below) demonstrate the selectivity and sensitivity of this tandem mass spectrometry methodology for the measurement of WP1244 in murine plasma and tissue samples.

TABLE 2

Summary of the in vitro antitumor activity of selected compounds.

| Compound | U87 IC$_{50}$ (nM) | Colo357-FG IC$_{50}$ (nM) | D54 IC$_{50}$ (nM) | H441 IC$_{50}$ (nM) |
|---|---|---|---|---|
| DNR | 142.6 | 46.4 | 231.4 | 15.92 |
| WP1244 | 0.20 | 3.1 | 1.08 | 0.91 |
| WP1243 | 8.3 | 76.2 | — | — |
| WP1245 | 0.23 | 27.3 | — | — |
| WP1248 | 1.1 | 4.7 | 2.61 | 5.7 |
| WP1249 | 7.7 | 51.2 | — | — |
| WP1276 | 27.8 | 443.0 | — | — |
| WP1277 | 105.4 | 4238.0 | — | — |

Example 3

Figure 5:
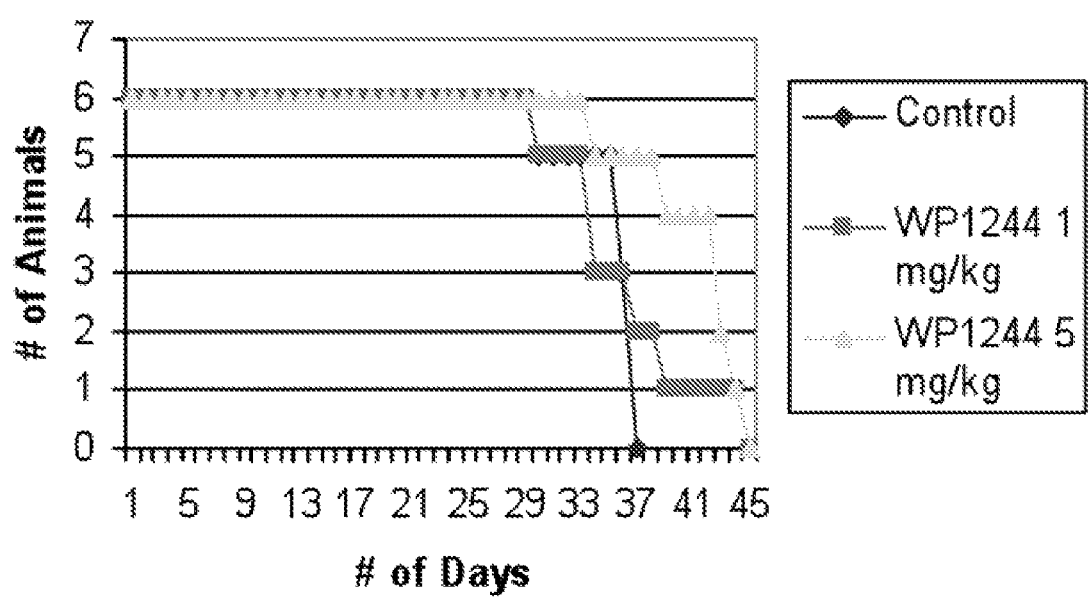
FIG. 5—Results from in vivo evaluation of WP1244 in U87 orthotopic models of glioblastoma multiforme.

In Vivo Evaluation of WP1244 in U87 Orthotopic Models of Glioblastoma Multiforme In vivo procedure—A mouse orthotopic xenograft brain glioma model was used to test WP1244 under the institutional guidelines for animal experimentation. Briefly, Passaged U87 MG cells 10-20×10$^6$ per dish (150 mm) were grow in 25 mL of DMEM/F$_{12}$ with 10% FBS. From this culture cells were diluted into a volume of 10 µL containing 1×10$^6$ U87 MG high-grade glioma cells and injected into the brains of NuNu athymic nude mice. The cells were implanted in the right putamen via a screw-guide system. In the case of WP1244, there were three groups of six animals each and the animals were treated with either control, 1 mg/kg of animal weight or 5 mg/kg of animal weight. All animals were treated 5 days after the implantation of tumor cells through i.p. route. The experiment was terminated after all subject animals had expired and Kaplan-Meier survival curves were generated. The results are shown in FIG. 5.

Example 4

Synthesis of DNA Binding Agents

Synthesis of minor groove binder moiety—Synthesis of methyl 4-(4-amino-1-methyl-1H-pyrrole-2-carboxamido)-1-methyl-1H-pyrrole-2-carboxylate.

Synthesis of 2,2,2-trichloro-1-(1-methyl-1H-pyrrol-2-yl)ethanone:

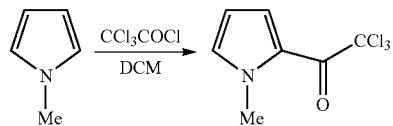

Solution of N-methyl pyrrole (20 g, 0.246 mol, 22 mL) in dichloromethane (100 mL) was added to the vigorously stirred solution of trichloroacetyl chloride (0.258 mol, 47 g, 29 mL) in dichloromethane. The reaction mixture was stirred at room temperature for 24 hr, then solvent was evaporated to dryness, and residue was purified by chromatography using silica gel column. Product was eluted with dichloromethane. Fractions contained product were pooled together and evaporated to give 35.5 g of pale yellow solid (yield 61%). NMR (δ, CDCl$_3$, ppm) 7.51 (dd, 1H, J=4.4 Hz, J=1.6 Hz, H-5), 6.97 (dd, 1H, J=J=2.0 Hz, H-3), 6.23 (dd, 1H, J=4.4 Hz, J=2.4 Hz, H-4), 3.98 (s, 3H, N-Me).

Synthesis of methyl 2,2,2-trichloro-1-(1-methyl-4-nitro-1H-pyrrol-2-yl)ethanone:

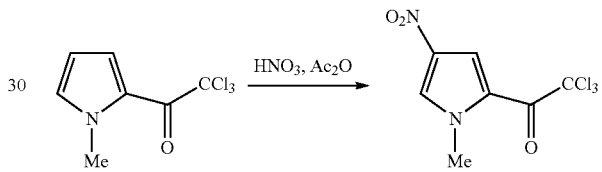

2,2,2-trichloro-1-(1-methyl-1H-pyrrol-2-yl)ethanone (35.4 g, 0.157 mol) was dissolved in acetic anhydride (200 mL). Obtained solution was cooled down to −40° C. Nitric acid (d=1.5 g/mL, 1.8 eq, 14 mL) was added over period of 30 minutes. The reaction mixture was allowed to warm-up to room temperature, and stirring was continued for additional 2 hrs. The mixture was cooled down to −20° C., then addition of isopropyl alcohol resulted in precipitation of the product which was then filtered off and washed with isopropyl alcohol. $^1$H-NMR (δ, CDCl$_3$, ppm) 7.91 (bs, 1H, H-5), 7.76 (bs, 1H, H-3), 4.04 (s, 3H, Me).

Synthesis of methyl 1-methyl-4-nitro-1H-pyrrole-2-carboxylate:

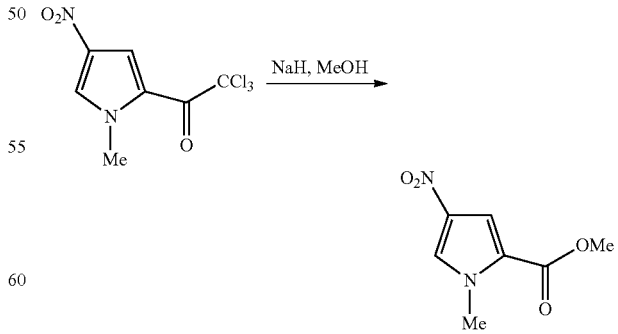

A solution of 2,2,2-trichloro-1-(1-methyl-4-nitro-1H-pyrrol-2-yl)ethanone (24 g, 87 mmol) in methanol (75 mL) was added dropwise to the suspension of NaH (300 mg) in methanol (30 mL). The reaction mixture was stirred at room temperature for 2 hr, then the reaction was quenched by addition of concentrated sulfuric acid (0.75 mL). The reaction mixture was then heated to reflux and allowed to slowly cool to room temperature. Product crystallized from reaction mixture as white needles. Product was filtered and dried under vacuum. ¹H NMR (δ, DMSO-d₆, ppm) 8.27 (bs, 1H, H-5), 7.31 (bs, 1H, H-3), 3.93, 3.80 (2s, 3H ea, Me).

Synthesis of 1-methyl-4-nitro-1H-pyrrole-2-carboxylic acid:

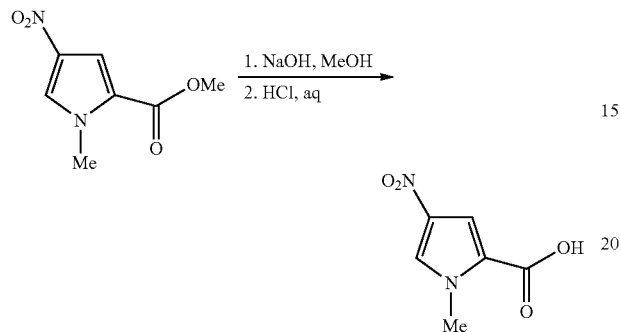

4-Nitro-1-methyl-pyrrole-2-carboxylate methyl ester (5 g, 27.15 mmol) was suspended in ethanol (70 mL). Solution of NaOH (3.2 g, 80 mmol) in water (50 mL) was added and resulting mixture was stirred at room temperature for 17 hrs. The reaction mixture was evaporated to dryness. 6N HCl (13.5 mL, 81 mmol) was added, and the mixture was stirred at room temperature for 15 minutes. Obtained white solid product was filtered, washed with water and dried under reduced pressure. 1-Methyl-4-nitro-1H-pyrrole-2-carboxylic acid (4.36 g) was obtained with a yield of 94%. ¹H NMR (δ, DMSO-d₆, ppm) 13.1 (bs, 1H, COOH), 7.24 (d, 1H, J=2.1 Hz, H-5), 8.21 (d, 1H, J=2.1 Hz, H-3), 3.90 (s, 3H, N-Me).

Synthesis of methyl 4-(1-methyl-4-nitro-1H-pyrrole-2-carboxamido)-1-methyl-1H-pyrrole-2-carboxylate:

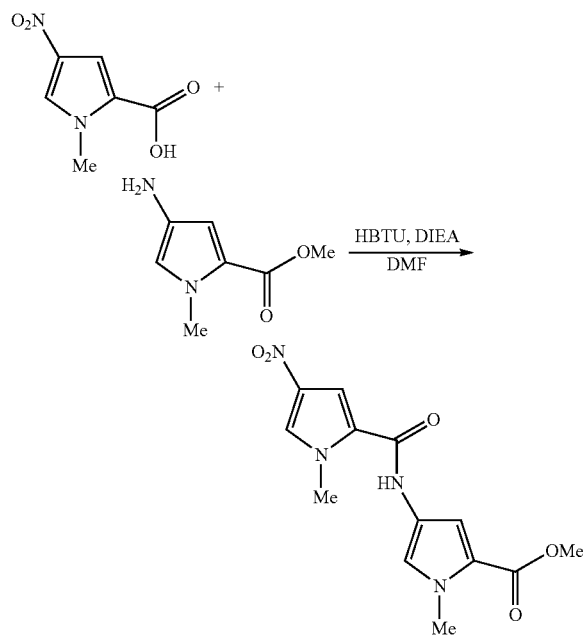

Diisopropylethylamine (4.91 mL, 28.18 mmol) was added to a solution of 4-nitro-1-methylpyrrole-carboxylic acid (1.92 g, 11.28 mmol) and HBTU (O-benzotriazole-N,N,N',N',-tetramethyl-uronium-hexafluoro-phosphate) (4.28 g, 11.28 mmol) in dry DMF (25 mL). Obtained brown solution was stirred for 20 min, then it was poured into the flask containing 4-amino-1-methylpyrrolecarboxylic acid methyl ester (1.74 g, 11.29 mmol). Resulting reaction mixture was stirred under N₂ for 18.5 hr. Precipitation appeared during reaction. Crystals were collected and washed with small amount of DCM, to give 2.13 g of pure product with yield of 61.6%; ¹H NMR (δ, acetone-d₆, ppm) 7.93 (d, 1H, J=3.2 Hz, H-2'), 7.44 (d, 1H, J=3.2 Hz, H-4'), 7.39 (d, 1H, J=3.2 Hz, H-2), 6.94 (d, 1H, J=3.2 Hz, H-4), 4.06, 3.91, 3.76 (3s, 3H ea, Me).

Synthesis of methyl 4-(4-amino-1-methyl-1H-pyrrole-2-carboxamido)-1-methyl-1H-pyrrole-2-carboxylate:

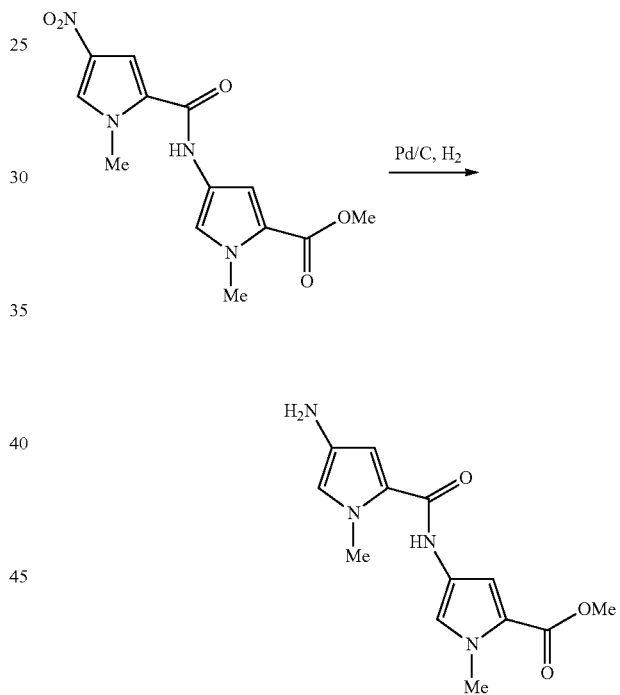

Pd/C (10%) (179 mg) was added to the dispersion of methyl 1-methyl-4-(1-methyl-4-nitro-1H-pyrrole-2-carboxamido)-1H-pyrrole-2-carboxylate (0.48 g, 1.56 mmol) in the mixture of ethyl acetate : methanol (1:1, v/v) (100 mL). Obtained mixture was subjected to hydrogenation in Parr apparatus (H₂, 30 psi). After 24 hr reaction was completed, catalyst was filtered off, and solvents were evaporated to dryness to give pure product with ~100% yield. ¹H-NMR (δ, CDCl₃, ppm) 8.02 (bs, 1H, NH), 6.75 (d, 1H, J=2.0 Hz), 6.29 (d, 1H, J=2.0 Hz), 6.22 (d, 1H, J=2.0 Hz), 3.84, 3.81, 3.78 (3s, 3H ea, Me), 3.28 (bs, 2H, NH₂).

Synthesis of methyl 1-methyl-4-(1-methyl-1H-pyrrole-2-carboxamido)-1H-pyrrole-2-carboxyamido)-1H-2-carboxylic acid:

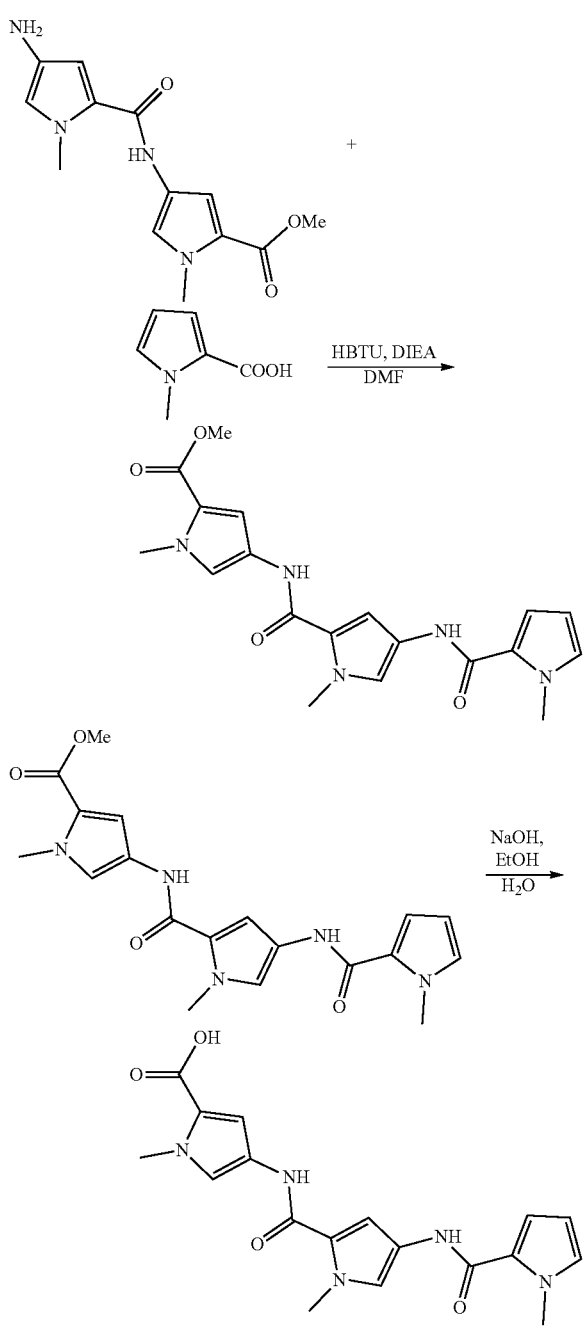

1-Methyl-2-pyrrole-carboxylic acid (297 mg, 2.37 mmol) and HBTU (893 mg, 2.35 mmol) were dissolved in anhydrous DMF (5 mL). N,N-diisopropylethylamine (DIEA) (0.68 mL, 7.9 mmol) was added and obtained solution was stirred at room temperature for 20 min, then it was added to previously prepared solution of methyl 4-(4-amino-1-methyl-1H-pyrrole-2-carboxamido)-1-methyl-1H-pyrrole-2-carboxylate (1.56 mmol) in DMF (5 mL). Obtained solution was stirred at room temperature for 24 hr. Solvent was evaporated to dryness and residue was dissolve in DCM (50 mL), washed with water, and dried over anhydrous $Na_2SO_4$. Drying agent and solvent were removed and product was purified by column chromatography (hexanes/ethyl acetate gradient). Fractions contained product were pooled together and evaporated to give 534.5 mg of methyl 1-methyl-4-(1-methyl-4-(1-methyl-1H-pyrrole-2-carboxamido)-1H-pyrrole-2-carboxamido)-1H-pyrrole-2-carboxylate (Yield 89.3%)

Methyl 1-methyl-4-(1-methyl-4-(1-methyl-1H-pyrrole-2-carboxamido)-1H-pyrrole-2-carboxamido)-1H-pyrrole-2-carboxylate (513 mg, 1.33 mmol) was dissolved in ethanol (10 mL). Water solution of NaOH (0.506 M, 13.1 mL) was added and the reaction mixture was stirred at room temperature for 24 hr. Ethanol was removed by evaporation and pH of the remaining water solution was adjusted to 1-2 by addition of 6N HCl (6.0 mmol, 1.0 mL). Obtained solid was filtered, washed with water and dried under reduced pressure to give 411.3 mg of pale yellow solid of 1-methyl-4-(1-methyl-4-(1-methyl-1H-pyrrole-2-carboxamido)-1H-pyrrole-2-carboxamido)-1H-pyrrole-2-carboxylic acid, yield 83.7%. $^1H$ NMR ($\delta$, DMSO-$d_6$, ppm), 9.88, 9.82 (2s, 1H ea, NH), 7.40 (d, 1H, J=1.8 Hz), 7.22 (d, 1H, J=1.8 Hz), 7.03 (d, 1H, J=1.8 Hz), 6.94 (dd, 1H, J=2.1 Hz, J=1.8 Hz), 6.90 (dd, 1H, J=3.9 Hz, J=1.8 Hz), 6.85 (d, 1H, J=2.0 Hz), 6.06 (dd, 1H, J=3.9 Hz, J=2.6 Hz), 3.87, 3.84, 3.82 (3s, 3H ea, N-Me).

Synthesis of 1-methyl-4-(1-methyl-4-(1-methyl-1H-imidazole-2-carboxamido)-1H-pyrrole-2-carboxamido)-1H-pyrrole-2-carboxylic acid:

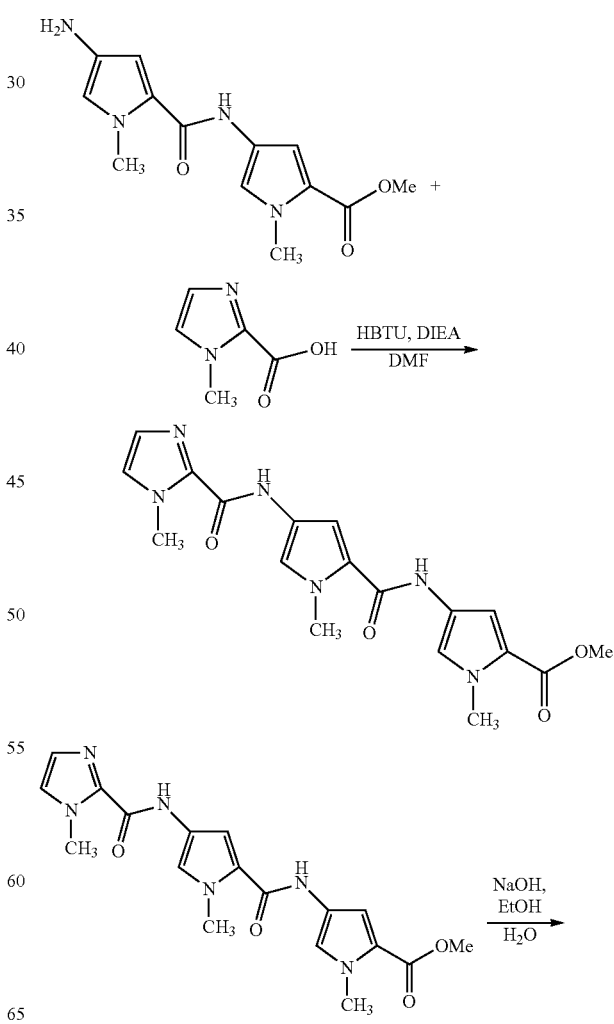

-continued

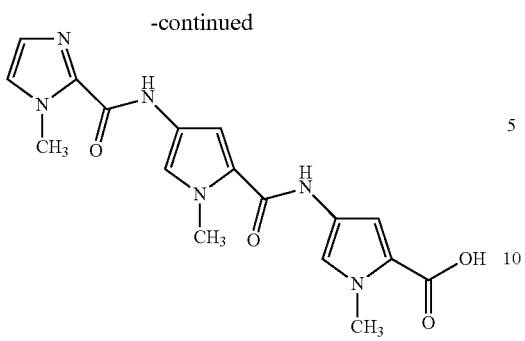

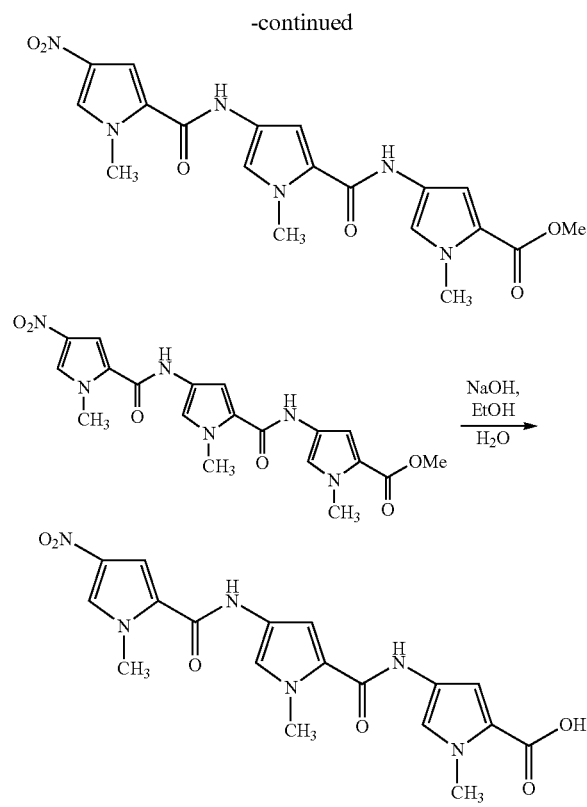

1-methyl-1H-imidazole-2-carboxylic acid (259 mg, 2.05 mmol) and HBTU (753 mg, 1.98 mmol) were dissolved in anhydrous DMF (4 mL). N,N-diisopropylethylamine (DIEA) (0.57 mL, 3.27 mmol) was added and obtained solution was stirred at room temperature for 20 min, then it was added to previously prepared solution of methyl 4-(4-amino-1-methyl-1H-pyrrole-2-carboxamido)-1-methyl-1H-pyrrole-2-carboxylate (1.21 mmol) in DMF (5 mL). Obtained solution was stirred at room temperature for 24 hr. Solvent was evaporated to dryness and residue was dissolved in CHCl$_3$ (50 mL), washed with water, dried over anhydrous Na$_2$SO$_4$. Drying agent and solvent were removed and product was purified by column chromatography (hexanes/ethyl acetate gradient). Fractions contained product were pooled together and evaporated to give 386 mg of methyl 1-methyl-4-(1-methyl-4-(1-methyl-1H-imidazole-2-carboxamido)-1H-pyrrole-2-carboxamido)-1H-pyrrole-2-carboxylate with a yield of 76.6%.

Methyl 1-methyl-4-(1-methyl-4-(1-methyl-1H-imidazole-2-carboxamido)-1H-pyrrole-2-carboxamido)-1H-pyrrole-2-carboxylate (338 mg, 0.879 mmol) was suspended in ethanol (11 mL). Water solution of NaOH (0.506 M, 8.7 mL) was added and the reaction mixture was stirred at 40° C. for 4.5 hr. Ethanol was removed by evaporation and pH of the remaining water solution was adjusted to 1-2 by addition of 6N HCl (6.0 mmol, 0.73 mL). Obtained solid was filtered, washed with water and dried under reduced pressure to give 307.7 mg of pale brown solid of 1-methyl-4-(1-methyl-4-(1-methyl-1H-imidazole-2-carboxamido)-1H-pyrrole-2-carboxamido)-1H-pyrrole-2-carboxylic acid with a yield of 94.5%. $^1$H NMR (δ, DMSO-d$_6$, ppm) 10.47, 9.93 (2s, 1H ea, NH), 7.42 (d, 1H, J=1.7 Hz), 7.28, 7.17, 7.07, 6.85 (4bs, 1H ea), 4.00, 3.84, 3.82 (3s, 3H ea, N-Me).

Synthesis of 1-methyl-4-(1-methyl-4-(1-methyl-4-nitro-1H-pyrrole-2-carboxamido)-1H-pyrrole-2-carboxamido)-1H-pyrrole-2-carboxylic acid:

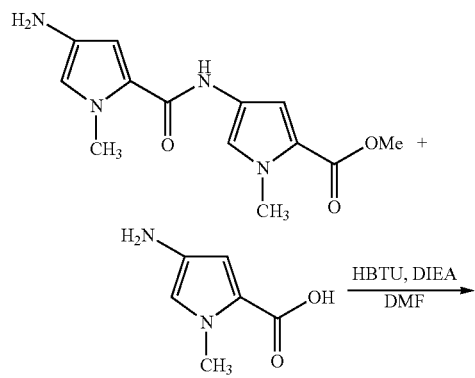

1-Methyl-4-nitro-1H-pyrrole-2-carboxylic acid (386 mg, 2.26 mmol) and HBTU (861 mg, 2.27 mmol) were dissolved in anhydrous DMF (5 mL). N,N-Diisopropylethylamine (DIEA) (0.66 mL, 3.78 mmol) was added and obtained solution was stirred at room temperature for 20 min, then it was added to previously prepared solution of methyl 4-(4-amino-1-methyl-1H-pyrrole-2-carboxamido)-1-methyl-1H-pyrrole-2-carboxylate (1.515 mmol) in DMF (5 mL). Obtained solution was stirred at room temperature for 24 hr. Solvent was evaporated to dryness then CHCl$_3$ (50 mL) was added to precipitate most of the product. Obtained yellow solid was washed with chloroform and dried under reduced pressure. 495.4 mg of methyl 1-methyl-4-(1-methyl-4-(1-methyl-4-nitro-1H-pyrrole-2-carboxamido)-1H-pyrrole-2-carboxamido)-1H-pyrrole-2-carboxylate was obtained with a yield of 76.3%.

Methyl 1-methyl-4-(1-methyl-4-(1-methyl-4-nitro-1H-pyrrole-2-carboxamido)-1H-pyrrole-2-carboxamido)-1H-pyrrole-2-carboxylate (495 mg, 1.15 mmol) was suspended in ethanol (16 mL). Water solution of NaOH (0.506 M, 11.5 mL) was added and the reaction mixture was stirred at 60-65° C. for 15 h. Ethanol was removed by evaporation and pH of the remaining water solution was adjusted to 1-2 by addition of 6N HCl (6.0 mmol, 1.0 mL). Obtained yellow solid was filtered, washed with water and dried under reduced pressure to give 473.6 mg of methyl 1-methyl-4-(1-methyl-4-(1-methyl-4-nitro-1H-pyrrole-2-carboxamido)-1H-pyrrole-2-carboxamido)-1H-pyrrole-2-carboxylate, yield 99.4%. $^1$H NMR (δ, DMSO-d$_6$, ppm) 10.27, 9.92 (2s, 1H ea, NH), 8.17 (d, 1H, J=1.8 Hz), 7.57 (d, 1H, J=1.8 Hz), 7.4 (d, 1H, J=1.8 Hz), 7.2 (d, 1H, J=1.8Hz), 7.03 (d, 1H, J=1.8 Hz), 6.83 (d, 1H, J=1.8 Hz), 3.94, 3.84, 3.81 (3s, 3H ea, N-Me).

Synthesis of 4-(4-(4-formamido-1-methyl-1H-pyrrole-2-carboxamido)-1-methyl-1H-pyrrole-2-carboxamido)-1-methyl-1H-pyrrole-2-carboxylic acid

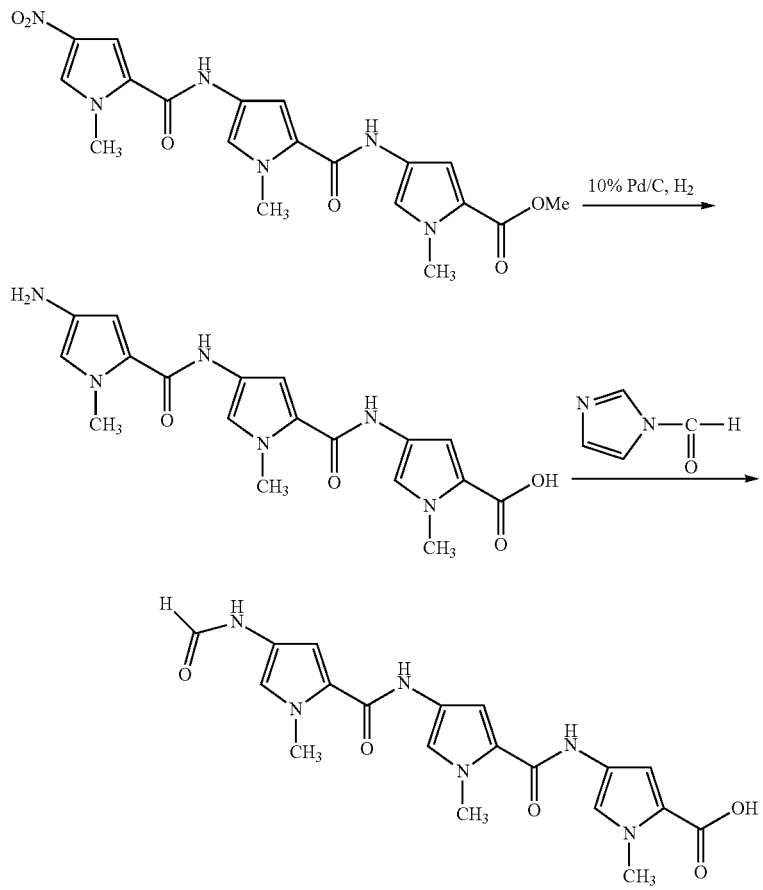

1-methyl-4-(1-methyl-4-(1-methyl-4-nitro-1H-pyrrole-2-carboxamido)-1H-pyrrole-2-carboxamido)-1H-pyrrole-2-carboxylic acid (519 mg, 1.25 mmol) was suspended in 1M water solution of $Na_2CO_3$ (75 mL) and DMF (25 mL), followed by addition of 10% Pd/C (wet, 50% $H_2O$, 201 mg), and then mixture was hydrogenated using Parr apparatus ($H_2$, p=20 psi) overnight. The reaction mixture was filtered through Celite®. Filtrate was evaporated to dryness and obtained residue was dissolved in the mixture of $CHCl_3$: MeOH (1:1, v/v) (2 mL) and without further purification was used in the next step of the process.

98% Formic acid (0.1 mL, 2.60 mmol) was added to the solution of carbonyldiimidazole (429 mg, 2.64 mmol) in dry THF (1.5 mL). The mixture was stirred at room temperature for 20 min, and was added to previously prepared and cooled to 0° C., solution of 4-(4-(4-amino-1-methyl-1H-pyrrole-2-carboxamido)-1-methyl-1H-pyrrole-2-carboxamido)-1-methyl-1H-pyrrole-2-carboxylic acid. Reaction mixture was stirred for 30 min, then it was concentrate to dryness. Ethyl acetate was added to precipitate the product. Brown solid of 4-(4-(4-formamido-1-methyl-1H-pyrrole-2-carboxamido)-1-methyl-1H-pyrrole-2-carboxamido)-1-methyl-1H-pyrrole-2-carboxylic acid (186.6 mg, yield 36.2%) was separated and dried under reduced pressure. ($^1$H NMR (δ, DMSO-$d_6$, ppm) 10.06 (s, 1H, H—CO), 9.19, 9.86 (2s, 1H ea, NH), 8.12 (d, 1H, J=1.8 Hz), 7.37 (d, 1H, J=1.8 Hz), 7.22 (d, 1H, J=1.8 Hz), 7.03 (d, 1H, J=1.8 Hz), 6.9 (d, 1H, J=1.8 Hz), 6.79 (d, 1H, J=1.8 Hz), 3.84 (s, 6H, NMe), 3.82 (s, 3H, NMe).

Synthesis of 1-methyl-4-(1-methyl-1H-pyrrole-2-carboxamido)-1H-pyrrole-2-carboxylic acid:

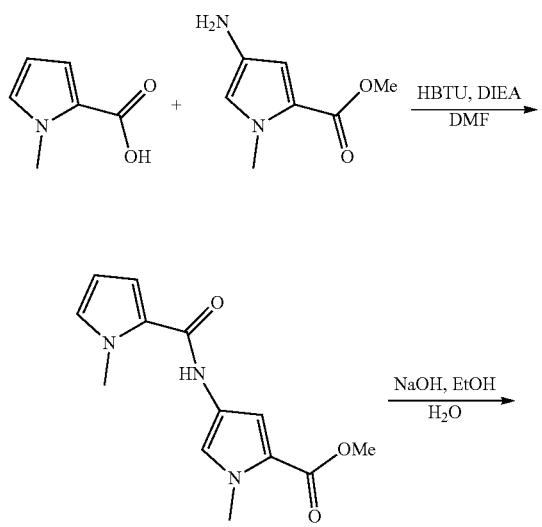

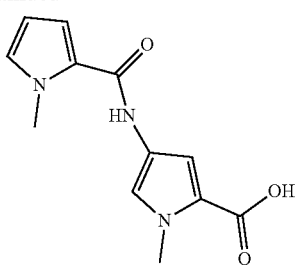

1-methyl-1H-pyrrole-2-carboxylic acid (890 mg, 7.14 mmol) and HBTU (2.7 g, 7.14 mmol) were dissolved in anhydrous DMF (15 mL). N,N-Diisopropylethylamine (DIEA) (3.1 mL, 17.8 mmol) was added and obtained solution was stirred at room temperature for 20 min, then it was added to previously prepared solution of methyl 4-amino-1-methyl-1H-pyrrole-2-carboxylate (7.14 mmol) in DMF (5 mL). Obtained solution was stirred at room temperature for 24 hr.

Solvent was evaporated to dryness and residue was dissolve in DCM (75 mL), washed with water, dried over anhydrous $Na_2SO_4$. Drying agent and solvent were removed and product was purified by column chromatography (hexanes/ethyl acetate gradient). Fractions contained product were pooled together and evaporated to give 1.69 g of methyl 1-methyl-4-(1-methyl-1H-pyrrole-2-carboxamido)-1H-pyrrole-2-carboxylate with a yield of 90%.

Methyl 1-methyl-4-(1-methyl-1H-pyrrole-2-carboxamido)-1H-pyrrole-2-carboxylate (1.68 g, 6.43 mmol) was suspended in ethanol (16 mL). Water solution of NaOH (0.506 M, 14 mL) was added and the reaction mixture was stirred at 60-65° C. for 3 hr. Ethanol was removed by evaporation and pH of the remaining water solution was adjusted to 1-2 by addition of 6N HCl (6.0 mmol, 2.0 mL). Obtained white solid was filtered, washed with water and dried under reduced pressure to give 1.52 g of 1-methyl-4-(1-methyl-1H-pyrrole-2-carboxamido)-1H-pyrrole-2-carboxylic acid. (yield 95%) $^1$H NMR (δ, DMSO-$d_6$, ppm) 12.1 (bs, 1H, COOH), 9.78 (bs, 1H, NH), 7.42 (d, 1H, J=2.0 Hz), 6.94 (dd, 1H, J=2.1 Hz, J=1.8 Hz), 6.90 (dd, 1H, J=3.9 Hz, J=1.8 Hz), 6.83 (d, 1H, J=2.0 Hz), 6.06 (dd, 1H, J=3.9 Hz, J=2.5 Hz), 3.87, 3.83 (2s, 3H ea, NMe).

Synthesis of 3'-(4"-aminobenzylo)-daunorubicin:

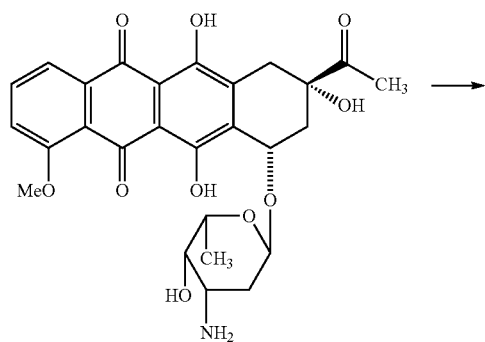

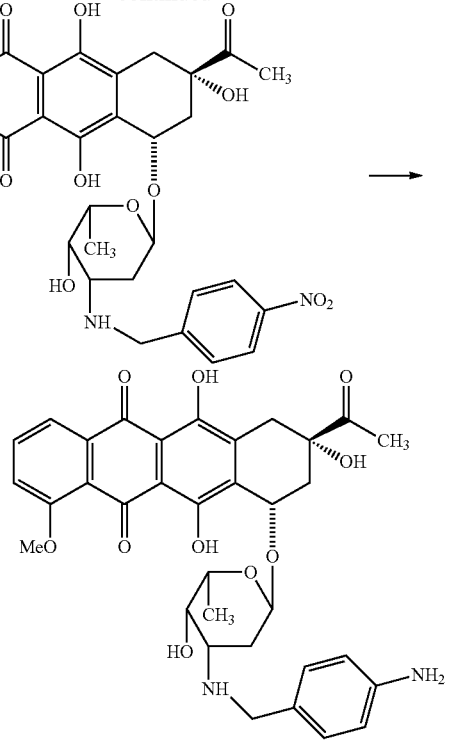

The mixture of daunorubicin hydrochloride (564 mg, 1 mmol), 4-nitrobenzyl bromide (216 mg, 1 mmol) in DMF (5 mL) was prepared. Sodium carbonate (255 mg, 2.40 mmol) was added and the reaction mixture was stirred at room temperature overnight. After reaction was completed the reaction mixture was diluted with DCM (50 mL), washed with water until neutral and dried over anhydrous sodium sulfate. Drying agent was filtered off, solvent was evaporated and product was purified by column chromatography (silica gel, using toluene/acetone gradient). Fractions containing product were pooled together and evaporated to give 490 mg of 3'-(4-nitro)benzyl-daunorubicin. Yield 73.9% $^1$H-NMR (δ, DMSO-$d_6$, ppm) 13.99, 13.2 (2bs, 1Hea 6,11-OH), 8.15 (ddd, 1H, J=J=1.9 Hz, H-2" or 6"), 8.12 (ddd, 1H, J=J=1.9 Hz, H-2" or 6"), 8.03 (dd, 1H, J=7.7 Hz, J=1.1 Hz, H-1), 7.79 (dd, 1H, J=8.4 Hz, J=7.8 Hz, H-2), 7.46 (bs, 1H, H-3" or 5"), 7.43 (bs, 1H, H-3" or 5"), 7.40 (dd, 1H, J=8.4 Hz, J=0.9 Hz, H-3), 5.52 (bs, 1H, H-7), 5,28 (dd, 1H, J=4.1 Hz, J=2.3 Hz, H-1'), 4.09 (s, 3H, OMe), 4.07 (q, 1H, J=6.6 Hz, H-5'), 3.91 (d, 1H, J=14.0 Hz, $CH_2$-Ph), 3.28 (d, 1H, J=14.0 Hz, $CH_2$-Ph), 3.66 (bs, 1H, H-4'), 3.22 (dd, 1H, J=18.0 Hz, J=1.7 Hz, H-10), 2.94 (d, 1H, J=18 Hz, H-10), 2.41 (s, 3H, 14-$CH_3$), 2.36 (d, 1H, J=14.8 Hz, H-8), 2.10 (dd, 1H, J=14.8 Hz, J=4.2 Hz, H-8), 1.82-1.75 (m, 2H, H-2'a, 2'e), 1.36 (d, 3H, J=6.6 Hz, H-6').

3'-(4-nitro)benzyl-daunrubicin (490 mg, 0.74 mmol) was dissolved in the mixture of methanol and DCM (1:1, v/v, 74 mL). Tin (II) chloride dihydrate (8.17 g, 36.2 mmol) was added and the reaction mixture was stirred at room temperature for 24 h. The reaction mixture was diluted with chloroform (100 mL), and it was poured into saturated solution of sodium bicarbonate (750 mL). Obtained mixure was stirred vigorously for 4 h, then it was filtered through Celite®. Layers were separated. Organic layer was washed with water until neutral, then it was dried over sodium sulfate. Drying agent and solvents were removed and product was purified by column chromatography (Silica gel, chloroform/methanol gradient was used as eluent). Fractions containing product were pooled together and evaporated to dryness to give 303 mg of 3'-(4-amino)benzyl-daunrubicin. Yield 64.8% $^1$H-NMR (δ, DMSO-$d_6$, ppm): 8.05 (d, 1H, J=7.6 Hz, H-1), 7.79 (dd, 1H, J=8.4 Hz, J=7.8 Hz, H-2), 7.41 (dd, 1H, J=8.5 Hz, J=7.6 Hz, H-3), 7.07, 7.04, 6.62, 6.59 (4 bs, 1H ea, H from aromatic linker), 5.53 (d, 1H, J=3.3 Hz, H-1'), 5.30 (bs, 1H, H-7), 4.69 (bs, 1H, 9-OH), 4.10 (s, 3H, OMe), 4.07 (q, 1H, J=6.6 Hz, H-5'), 3.72 (d, 1H, J=12.5 Hz, CH$_2$-Ph), 3.69 (bs, 1H, H-4'), 3.58 (d, 1H, J=12.5 Hz, CH$_2$-Ph), 3.24 (d, 1H, H -10), 2.98 (d, 1H, H-10), 3.03-2.95 (m, 1H, H-3'), 2.44 (s, 3H, 14-CH$_3$), 2.39 (d, 1H, J=14.0 Hz, H-8), 2.11 (dd, 1H, J=14.0 Hz, J=4.0 Hz, H-8), 1.84 (ddd, 1H, J=J=13.0 Hz, J=3.7 Hz, H-2'a), 1.68 (dd, 1H, J=13.0 Hz, J=4.8 Hz, H-2'e), 1.39 (d, 3H, J=6.6 Hz, H-6').

Synthesis of WP1244:

DMF (0.5 mL). Final reaction mixture was stirred under nitrogen for 98 h. DMF was evaporated under reduced pressure at 65° C. Residue was dissolved in the mixture of chloroform:methanol (95:5, v/v, 5 mL) and obtained solution was applied on top of chromatography column. Product was eluted with chloroform/methanol gradient. Fraction containing product were pooled together and evaporated to give red solid. Product was additionally precipitated using chloroform/hexanes system. 69.1 mg of WP1244 (yield 62.7%) was obtained. $^1$H-NMR (δ, CDCl$_3$, ppm) 13.95 (bs, 1H, 6 or 11 OH), 9.80 (bs, 1H, NH), 8.56 (d, 1H, J=4.3 Hz), 8.24 (d, 1H, J=7.78 Hz), 7.98 (d, 1H, J=7.68 Hz), 7.88 (dd, 1H, J=J=7.6 Hz), 7.76-7.70 (m, 3H), 7.47-7.44 (m, 3H), 7.34 (d, 1H, J=8.5 Hz), 7.30-7.05 (m, 4H), 6.88, 6.73 (2s, 1H, ea), 5.49 (bs, 1H), 5.25 (bs, 1H), 4.69 (bs, 1H), 4.08 (q, 1H, J=6.8 Hz), 4.05, 3.94, 3.87 (3s, 3Hea), 3.77 (d, 1H, J=13.0 Hz), 3.67 (bs, 1H), 3.63 (d, 1H, J=13.0 Hz), 3.20 (d, 1H, J=18.9 Hz), 3.04-2.88 (m, 2H, H-10), 2.38 (d, 1H, J=15.0 Hz), 2.08

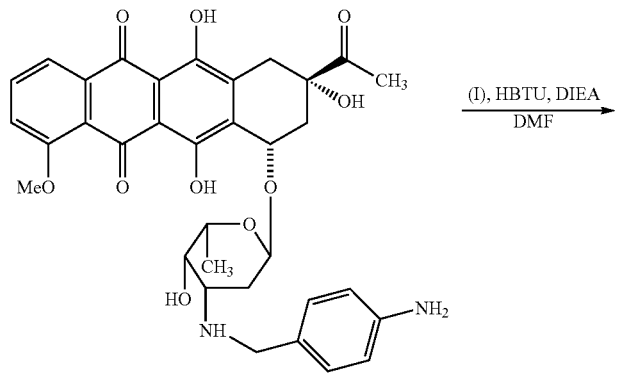

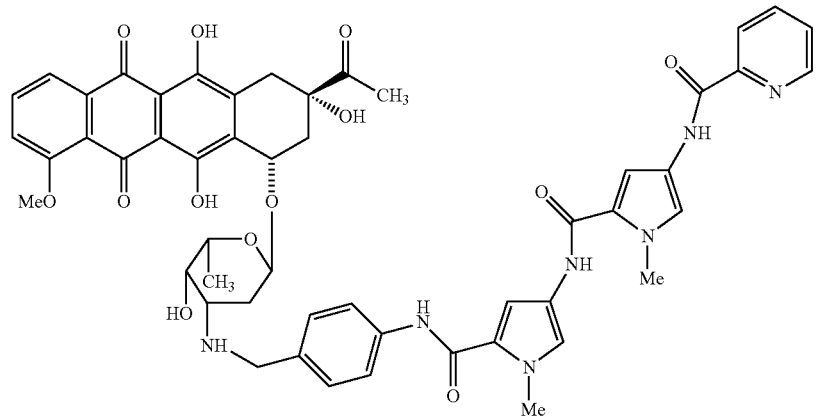

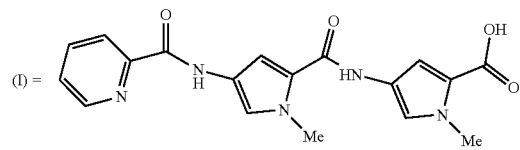

3'-(4-amino)benzylo-daunorubicin (124.5 mg, 0.338 mmol) and HBTU (134.3 mg, 0.354 mmol) were dissolved in dry DMF (1 mL). Diisopropylethylamine (0.078 mL, 0.448 mmol) was added and obtained solution was stirred at room temperature for 30 min, then it was added to the solution of linker (1) (scheme above) (71 mg, 0.112 mmol) in (dd, 1H, J=15.0 Hz, J=3.8 Hz), 1.90-1.60 (m, 2H), 1.38 (d, 3H, J=6.4 Hz).

Using 3'-(4"-aminobenzylo)-daunorubicin and appropriate minor groove binding moiety the compounds characterized below were synthesized according to the procedure described above for WP1244.

WP1249:

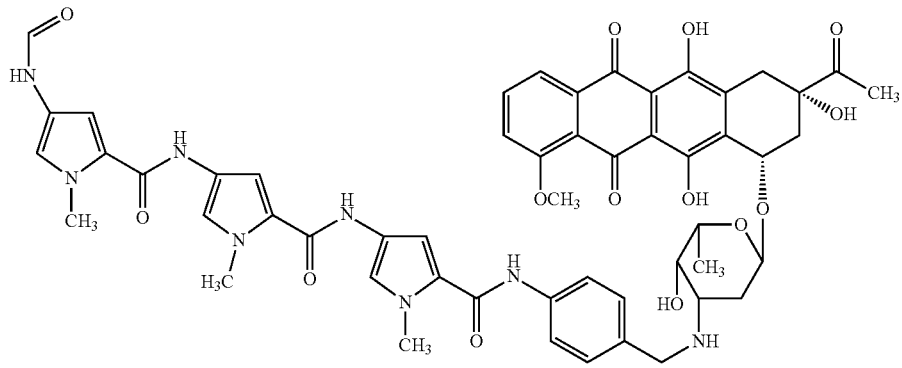

¹H NMR (δ, 10% of CD₃OD in CDCl₃, ppm) 8.13 (s, 1H, NH), 7.96 (d, 1H, J=7.5 Hz, H-1), 7.75 (dd, 1 H, J=J=8 Hz, H-2), 7.47 (d, 2H, J=8 Hz, H-3 and linker), 7.36 (d, 1H, J=8.5 Hz, linker), 7.19 (d, 2H, J=8.5 Hz, linker), 7.14 (d, 2H, J=10.5 Hz, linker), 7.03 (S, 1H, linker), 6.81 (s, 1H, linker), 6.78 (d, 2H, J=9.0 Hz, linker), 5.49 (s, 1H, H-1'), 5.22 (bs, 1H, H-7), 4.1 (q, 1H, J=6.5 Hz, H-5'), 4.04 (s, 3H, OMe), 3.89 (s, 1H, 9-OH), 3.88, 3.87, 3.84 (3s, 3H ea, N-Me, linker), 3.74 (d, 1H, J=13.0 Hz, CH₂), 3.69 (bs, 1H, H-4'), 3.65 (d, 1H, J=13.0 Hz, CH₂), 3.18 (d, 1H, J=18.5 Hz, H-10), 3.0-2.9 (m, 2H, H-3' and H-10), 2.41 (s, 3H, 14-CH₃), 2.34 (d, 1H, J=14.5 Hz, H-8), 2.08 (dd, 1H, J=14.5 Hz, J=4.0 Hz, H-8), 1.81 (d, 2H, H-2' a,e), 1.33 (d, 3H, J=6.5 Hz, H-6').

WP1276:

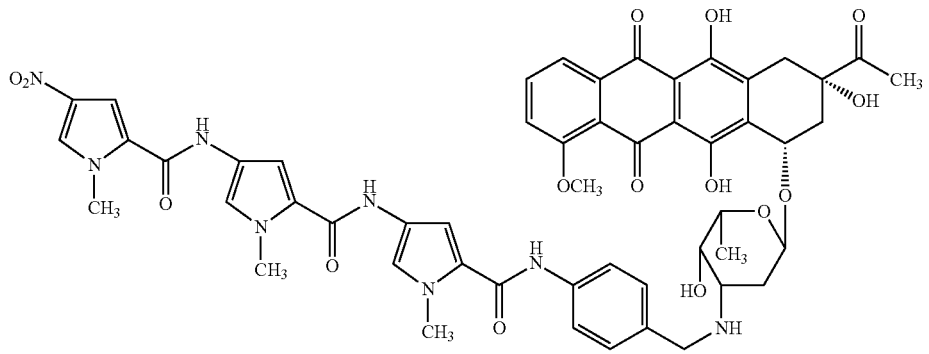

¹H NMR (δ, 10% of CD₃OD in CDCl₃, ppm) 8.03 (d, 1H, J=8.0 Hz, H-1), 7.79 (dd, 1H, J=J=8.0 Hz, H-2), 7.60 (bs, 1H, linker), 7.51 (d, 2H, J=8.5 Hz, linker), 7.41 (d, 1H, J=8.0 Hz, H-3), 7.35 (bs, 1H, linker), 7.25 (d, 2H, J=8.5 Hz, linker), 7.22 (d, 2H, J=10.0 Hz, linker), 6.83 (d, 1H, J=10.0 Hz, linker), 5.53 (bs, 1H, H-5.25 (bs, 1H, H-7), 4.12 (q, 1H, J=6.5 Hz, H-5'), 4.08, 4.03, 3.95, 3.90 (4s, 3H ea, OMe and N-Me linker), 3.87 (d, 1H, J=17.0 Hz, CH₂), 3.80 (d, 1H, J=17.0 Hz, CH₂), 3.76 (bs, 1H, H-4') 3.25-3.12 (m, 2H, H-10 and H-3'), 2.99 (d, 1H, J=19.0 Hz, H-10), 2.42 (s, 3H, 14-CH₃), 2.34 (d, 1H, J=14.5 Hz, H-8), 2.03 (dd, 1H, J=14.5 Hz, J=4.0 Hz, H-8), 1.96-1.83 (m, 2H, H-2' a,e), 1.80 (d, 3H, J=6.5 Hz, H-6').

WP1248:

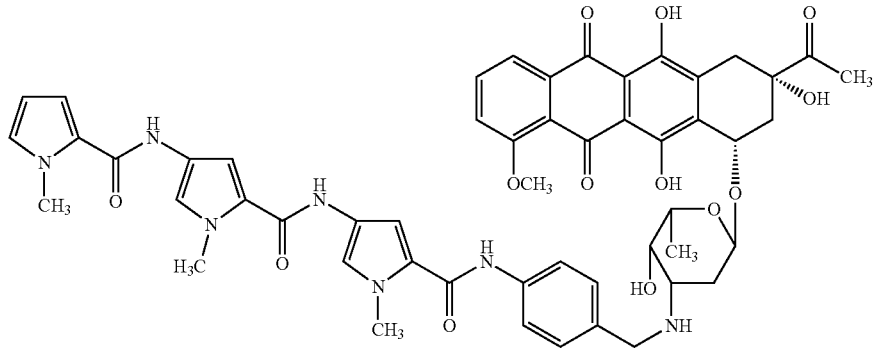

¹H NMR (δ, 5% of CD₃OD in CDCl₃, ppm) 7.93 (d, 1H, J=8.0 Hz, H-1), 7.70 (dd, 1H, J=J=8.0 Hz, H-2), 7.43 (m, 2H, linker), 7.32 (d, 2H, J=8.5 Hz, H-3), 7.17-7.14 (m, 3H, linker), 7.10 (bs, 1H, linker), 6.98 (d, 2H, J=7.0 Hz, linker), 6.75 (d, 2H, J=9.5 Hz, linker), 5.44 (bs, 1H, H-1'), 5.19 (bs, 1H, H-7), 4.03 (q, 1H, J=6.5 Hz, H-5'), 4.04, 4.00, 3.88, 3.82 (4s, 3H ea, OMe and N-Me linker), 3.69 (d, 1H, J=13.0 Hz, CH₂), 3.63 (bs, 1H, H-4'), 3.62 (d, 1H, J=13.0 Hz, CH₂), 3.14 (d, 2H, J=18.5 Hz, H-10), 2.91-2.87 (m, 2H, H-10 and H-3'), 2.33 (s, 3H, 14-CH₃), 2.32 (d, 1H, J=14.5 Hz, H-8), 2.03 (dd, 1H, J=14.5 Hz, J=4.0 Hz, H-8), 1.76-1.73 (m, 2H, H-2' a,e), 1.31 (d, 3H, J=6.5 Hz, H-6').

WP 1243:

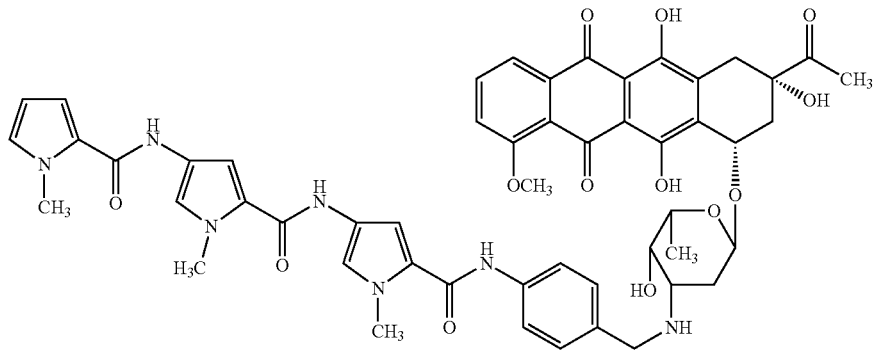

¹H NMR (δ, 5% of CD₃OD in CDCl₃, ppm) 7.99 (d, 1H, J=7.5 Hz, H-1), 7.76 (dd, 1H, J=J=8.0 Hz, H-2), 7.48 (m, 2H, linker), 7.37 (d, 2H, J=8.0 Hz, H-3), 7.20 (d, 2H, linker), 7.14 (bs, 1H, linker), 7.08 (bs, 1H, linker), 6.82-6.72 (m, 4H, linker), 6.11 (dd, 1H, J=3.9 Hz, J=2.7 Hz, linker), 5.50 (bs, 1H, H-1'), 5.30 (bs, 1H, H-7), 4.08 (q, 1H, J=6.5 Hz, H-5'), 4.06, 3.96, 3.91, 3.86 (4s, 3H ea, OMe and N-Me linker), 3.75 (d, 1H, J=13.0 Hz, CH₂), 3.73-3.65 (m, 2H, H-4', CH₂), 3.21 (d, 2H, J=18.5 Hz, H-10), 2.95-2.92 (m, 2H, H-10 and H-3'), 2.41 (s, 3H, 14-CH₃), 2.35 (d, 1H, J=14.5 Hz, H-8), 2.03 (dd, 1H, J=14.5 Hz, J=4.0 Hz, H-8), 1.76-1.73 (m, 2H, H-2' a,e), 1.35 (d, 3H, J=6.5 Hz, H-6').

WP1402:

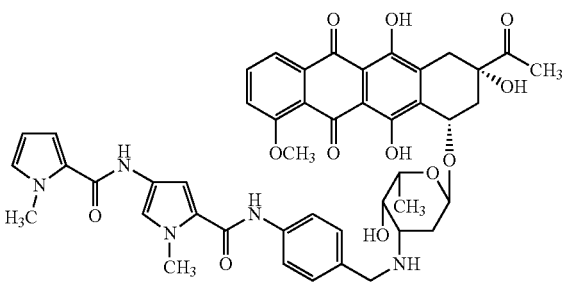

¹H NMR (δ, CDCl₃, ppm) 7.97 (dd, 1H, J=7.4 Hz, J=1.0 Hz, H-1), 7.72 (dd, 1H, J=J=8.2 Hz, H-2), 7.62 (bs, 1H, linker), 7.40 (d, 2H, J=J=8.2 Hz, linker), 7.34 (d, 1H, J=8.5 Hz, H-3), 7.17 (d, 2H, J=8.3 Hz, linker), 7.10 (bs, 1H, linker), 6.75 (bs, 1H, linker), 6.70 (bs, 1H, linker), 6.64 (d, 1H, J=2.7 Hz, linker), 6.10 (dd, 1H, J=3.8 Hz, J=2.6 Hz, linker), 5.50 (bs, 1H, H-1'), 5.24 (bs, 1H, H-7), 4.07 (q, 1H, J=6.7 Hz, H-5'), 4.04, (s, 3H, OMe), 3.96, 3.85 (2s, 3Hea, N-Me linker), 3.76 (d, 1H, J=12.9 Hz, CH₂), 3.67 (bs, 1H, H-4'), 3.62 (d, 1H, J=12.9 Hz, CH₂), 3.19 (d, 1H, J=18.8 Hz, H-10), 3.00-2.86 (m, 3H, H-3', H-10), 2.41 (s, 3H, 14 CH₃), 2.37 (d, 1H, J=14.9 Hz, H-8), 2.07 (dd, 1H, J=14.9 Hz, J=3.1 Hz, H-8), 1.88-1.64 (m, 2H, H-2' ae), 1.37 (d, 3H, J=6.7 Hz, H-6').

WP1277:

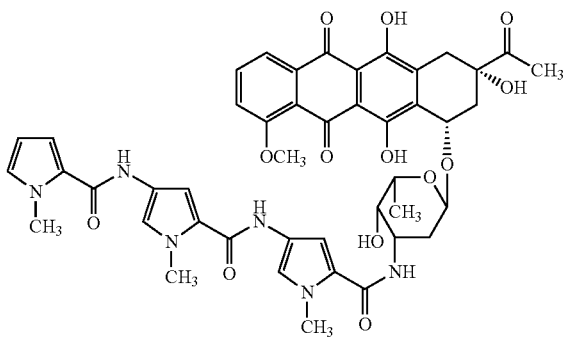

DIEA (0.054 mL, 0.308 mmol) was added to a solution of 1-methyl-4-(1-methyl-4-(1-methyl-1H-pyrrole-2-carboxamido)-1H-pyrrole-2-carboxamido)-1H-pyrrole-2-carboxylic acid (51 mg, 0.138 mmol) and HBTU (54 mg, 0.142 mmol) in anhydrous DMF (1 mL). Obtained mixture was stirred for 20 min, then it was added to a solution of daunorubicin hydrochloride (50 mg, 0.088 mmol) in DMF (0.5 mL). Obtained mixture was stirred at room temperature or 4.5 h. Chloroform (2 mL) was added and product was precipitated using hexanes. Crude solid product was purified by column chromatography using chloroform/methanol gradient as elution system. Fractions contained WP1277 were pooled together and evaporated to dryness. Additional precipitation (CHCl$_3$/Hexanes) gave pure red solid that was dried under reduced pressure. 61.4 mg of WP1277 was obtained with a yield of 79.3%. $^1$H NMR (δ, CDCl$_3$, ppm) 13.97, 13.26 (2s, 1H ea, 6-OH, 11-OH), 8.00 (d, 1H, J=7.5 Hz, H-1), 7.75 (dd, 1H, J=J=8.4 Hz, H-2), 7.60, 7.56 (2bs, 1H ea, linker), 7.33 (d, 2H, J=8.1 Hz, H-3), 7.09 (bs, 2H, linker), 6.75 (bs, 1H, linker), 6.67 (bs, 1H, linker), 6.61 (bs, 1H, linker), 6.51 (bs, 1H, linker), 6.25 (d, 1H, J=8.1 Hz, linker), 6.09 (dd, 1H, J=3.9 Hz, J=2.7 Hz, linker), 5.50 (bs, 1H, H-1'), 5.23 (bs, 1H, H-7), 4.26 (q, 1H, J=6.5 Hz, H-5'), 4.03, 3.96, 3.89, 3.8 (4s, 3H ea, OMe and N-Me linker), 3.70 (bs, 1H, H-4'), 3.24 (d, 1H, J=18.9 Hz, H-10), 2.94 (d, 1H, J=18.9 Hz, H-10), 2.53-2.40 (m, 1H, H-3'), 2.42 (s, 3H, 14-CH$_3$), 2.36 (d, 1H, J=14.5 Hz, H-8), 2.10 (dd, 1H, J=14.5 Hz, J=4.0 Hz, H-8), 1.90-1.80 (m, 2H, H-2' a,e), 1.30 (d, 3H, J=6.5 Hz, H-6').

WP1401:

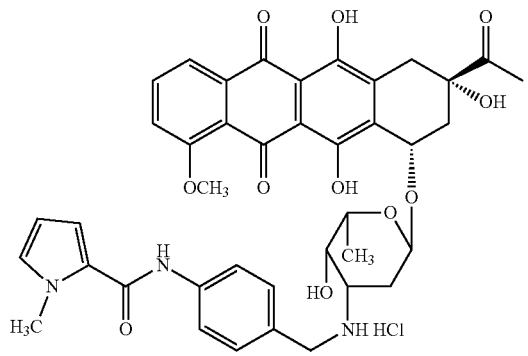

$^1$H NMR (δ, CDCl$_3$, ppm) 8.05 (dd, 1H, J=7.8 Hz, J=1.0 Hz, H-1), 7.46 (dd, 1H, J=J=7.8 Hz, H-2), 7.58 (bs, 1H, linker), 7.42 (dd, 3H, J=J=9.4 Hz, linker), 7.22 (d, 2H, J=8.4 Hz, linker), 6.77 (dd, 1H, J=J=2.0 Hz, linker), 6.68 (dd, 1H, J=4.1 Hz, J=1.4 Hz, linker), 6.14 (dd, 1H, J=4.0 Hz, J=2.5 Hz, linker), 5.53 (bs, 1H, H-1'), 5.30 (bs, 1H, H-7), 4.10 (q, 1H, J=6.0 Hz, H-5'), 4.09 (s, 3H, OMe), 3.96 (s, 3H, N-Me linker), 3.85 (d, 1H, J=12.8 Hz, CH$_2$), 3.75 (bs, 1H, H-4'), 3.73 (d, 1H, J=12.8 Hz, CH$_2$), 3.25 (d, 1H, J=18.5 Hz, H-10), 3.31-3.30 (m, 1H, H-3'), 2.99 (d, 1H, J=18.5 Hz, H-10), 2.44 (s, 3H, 14 CH$_3$), 2.39 (d, 1H, J=15.0 Hz, H-8), 2.11 (dd, 1H, J=15.0 Hz, J=4.5 Hz, H-8), 1.95-1.70 (m, 2H, H-2' ae), 1.39 (d, 3H, J=6.0 Hz, H-6').

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 6,673,907
U.S. Pat. No. 7,109,177
U.S. Pat. No. 7,557,090
PCT Publication WO 2008/029294
Bickel et al., *Adv. DrugDeliv. Rev.,* 46: 247-279, 2001.
*Handbook of Pharmaceutical Salts: Properties, and Use,* Stahl and Wermuth (Eds.), Verlag Helvetica Chimica Acta, 2002.
*March's Advanced Organic Chemistry: Reactions,* Mechanisms, and Structure, 2007.
Pardridge, *J. Neurovirol.,* 5: 556-569, 1999.
Young et al, *N Engl. J. Med.,* 312:692, 1985.

What is claimed is:
1. A compound of the formula:

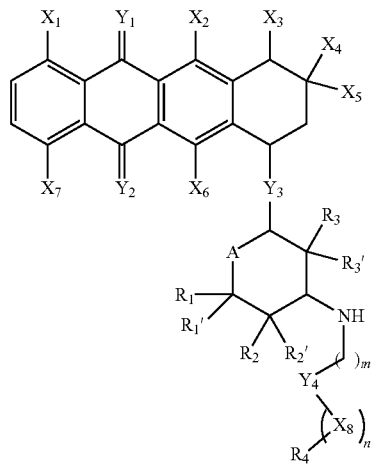

wherein:

$X_1$, $X_2$, $X_3$, $X_6$, and $X_7$ are each independently hydrogen, halo, hydroxy, carboxy, ester$_{(C \leq 12)}$, substituted ester$_{(C \leq 12)}$, alkoxy$_{(C \leq 12)}$, or substituted alkoxy$_{(C \leq 12)}$;

$X_4$ is acyl$_{(C \leq 18)}$ or substituted acyl$_{(C \leq 18)}$;

$X_5$ is hydrogen, hydroxy, alkoxy$_{(C \leq 12)}$, or substituted alkoxy$_{(C \leq 12)}$;

$Y_1$, $Y_2$, and $Y_3$ are each independently O, S, or NH;

A is O or S;

$R_1$, $R_1'$, $R_2$, $R_2'$, $R_3$, and $R_3'$ are each independently hydrogen, amino, halo, hydroxy, mercapto, or
  alkyl$_{(C \leq 8)}$, alkoxy$_{(C \leq 8)}$, alkylthio$_{(C \leq 8)}$, alkylamino$_{(C \leq 8)}$, dialkylamino$_{(C \leq 8)}$, or a substituted version of any of these groups;

$Y_4$ is a covalent bond; or
  arenediyl$_{(C \leq 12)}$, heteroarenediyl$_{(C \leq 12)}$, or a substituted version of either of these groups;

each $X_8$ is independently —$X_9$-heteroarenediyl$_{(C \leq 12)}$ or substituted —$X_9$-heteroarenediyl$_{(C \leq 12)}$, wherein:
  $X_9$ is —NHC(O)— or —C(O)NH—;

$R_4$ is hydrogen, amino, nitro, alkylamino$_{(C \leq 12)}$, dialkylamino$_{(C \leq 12)}$, amido$_{(C \leq 12)}$, substituted alkylamino$_{(C \leq 12)}$, substituted dialkylamino$_{(C \leq 12)}$, or substituted amido$_{(C \leq 12)}$;

m is 0, 1, 2, or 3; and n is 1, 2, or 3;

or a pharmaceutically acceptable salt thereof.

2. The compound of claim 1, wherein the formula is further defined as:

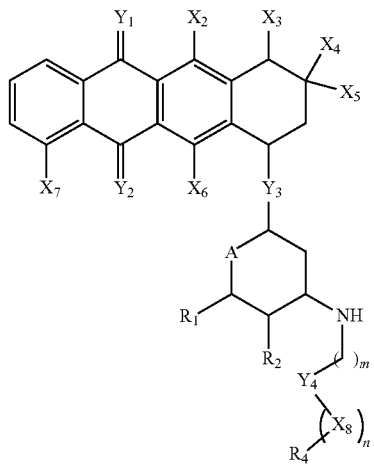

wherein:

$X_2$, $X_3$, $X_6$, and $X_7$ are each independently hydrogen, halo, hydroxy, carboxy, ester$_{(C \leq 12)}$, substituted ester$_{(C \leq 12)}$, alkoxy$_{(C \leq 12)}$, or substituted alkoxy$_{(C \leq 12)}$;

$X_4$ is acyl$_{(C \leq 18)}$ or substituted acyl$_{(C \leq 18)}$;

$X_5$ is hydrogen, hydroxy, alkoxy$_{(C \leq 12)}$, or substituted alkoxy$_{(C \leq 12)}$;

$Y_1$, $Y_2$, and $Y_3$ are each independently O, S, or NH;

A is O or S;

$R_1$ and $R_2$ are each independently hydrogen, amino, halo, hydroxy, mercapto, or
  alkyl$_{(C \leq 8)}$, alkoxy$_{(C \leq 8)}$, alkylthio$_{(C \leq 8)}$, alkylamino$_{(C \leq 8)}$, dialkylamino$_{(C \leq 8)}$, or a substituted version of any of these groups;

$Y_4$ is a covalent bond; or
  arenediyl$_{(C \leq 12)}$, heteroarenediyl$_{(C \leq 12)}$, or a substituted version of either of these groups;

each $X_8$ is independently —$X_9$-heteroarenediyl$_{(C \leq 12)}$ or substituted —$X_9$-heteroarenediyl$_{(C \leq 12)}$, wherein:
  $X_9$ is —NHC(O)— or —C(O)NH—;

$R_4$ is hydrogen, amino, nitro, alkylamino$_{(C \leq 12)}$, dialkylamino$_{(C \leq 12)}$, amido$_{(C \leq 12)}$, substituted alkylamino$_{(C \leq 12)}$, substituted dialkylamino$_{(C \leq 12)}$, or substituted amido$_{(C \leq 12)}$;

m is 0, 1, 2, or 3; and n is 1, 2, or 3;

or a pharmaceutically acceptable salt thereof.

3. The compound of claim 1, wherein the formula is further defined as:

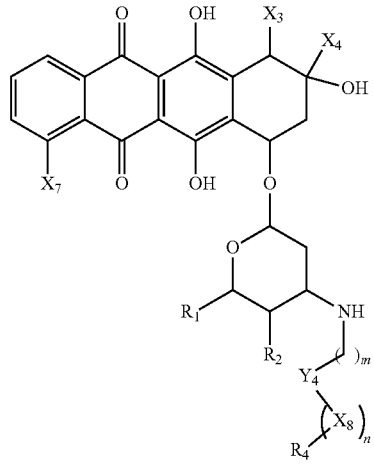

wherein:

$X_7$ is hydrogen, halo, hydroxy, carboxy, alkoxy$_{(C \leq 12)}$, substituted alkoxy$_{(C \leq 12)}$, ester$_{(C \leq 12)}$, or substituted ester$_{(C \leq 12)}$;

$X_4$ is acyl$_{(C \leq 18)}$ or substituted acyl$_{(C \leq 18)}$;

$R_1$ and $R_2$ are each independently hydrogen, amino, halo, hydroxy, mercapto, or
  alkyl$_{(C \leq 8)}$, alkoxy$_{(C \leq 8)}$, alkylthio$_{(C \leq 8)}$, alkylamino$_{(C \leq 8)}$, dialkylamino$_{(C \leq 8)}$, or a substituted version of any of these groups;

$Y_4$ is a covalent bond, arenediyl$_{(C \leq 12)}$, heteroarenediyl$_{(C \leq 12)}$, or a substituted version of either of these groups;

each $X_8$ is independently —$X_9$-heteroarenediyl$_{(C \leq 12)}$ or substituted —$X_9$-heteroarenediyl$_{(C \leq 12)}$, wherein:
  $X_9$ is —NHC(O)— or —C(O)NH—;

$R_4$ is hydrogen, amino, nitro, alkylamino$_{(C \leq 12)}$, dialkylamino$_{(C \leq 12)}$, amido$_{(C \leq 12)}$, substituted alkylamino$_{(C \leq 12)}$, substituted dialkylamino$_{(C \leq 12)}$, or substituted amido$_{(C \leq 12)}$;

m is 0, 1, 2, or 3; and n is 1, 2, or 3;

or a pharmaceutically acceptable salt thereof.

4. The compound of claim 1, wherein $X_7$ is halo, alkoxy$_{(C \leq 12)}$ or substituted alkoxy$_{(C \leq 12)}$.

5. The compound of claim 1, wherein $X_4$ is acyl$_{(C \leq 8)}$ or substituted acyl$_{(C \leq 8)}$.

6. The compound of claim 5, wherein $X_4$ is —C(O)CH$_3$ or —C(O)CH$_2$OH.

7. The compound of claim 1, wherein $R_1$ is alkyl$_{(C \leq 8)}$ or substituted alkyl$_{(C \leq 8)}$.

8. The compound of claim 7, wherein $R_1$ is methyl.

9. The compound of claim 7, wherein $R_1$ is fluoromethyl, difluoromethyl, trifluoromethyl, or hydroxymethyl.

10. The compound of claim 1, wherein $R_2$ is hydroxy.

11. The compound of claim 1, wherein m is 1.
12. The compound of claim 1, wherein $Y_4$ is arenediyl$_{(C \leq 12)}$ or a covalent bond.
13. The compound of claim 1, wherein $X_8$ is —$X_9$-heteroarenediyl$_{(C \leq 12)}$.
14. The compound of claim 13, wherein $X_8$ is:

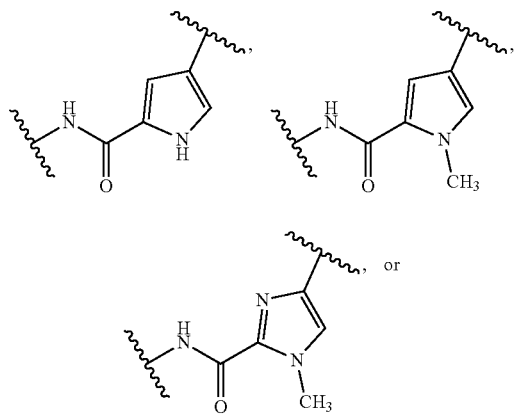

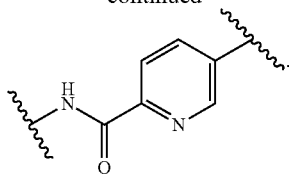

15. The compound of claim 14, wherein $X_8$ is:

16. The compound of claim 1, wherein $R_4$ is hydrogen, nitro, or amido$_{(C \leq 12)}$.
17. The compound of claim 1, wherein the compound is formulated as a pharmaceutically acceptable salt.
18. A compound selected from

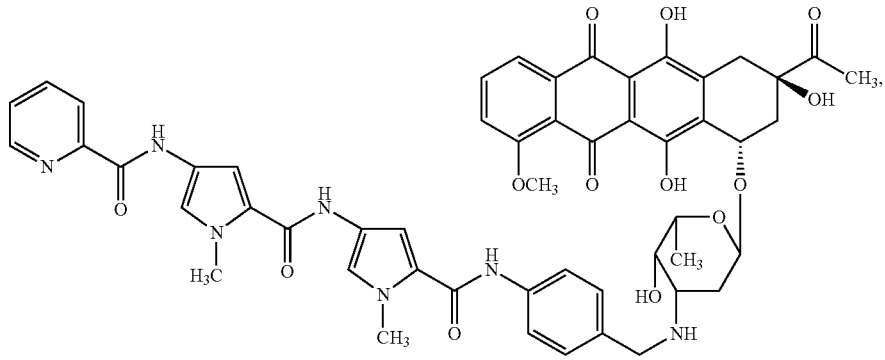

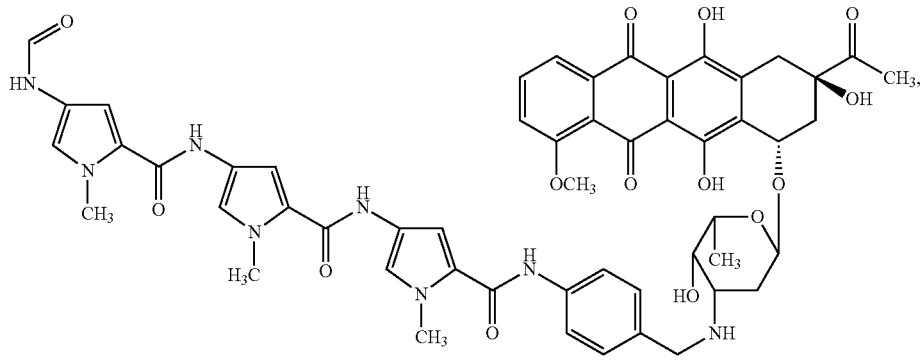

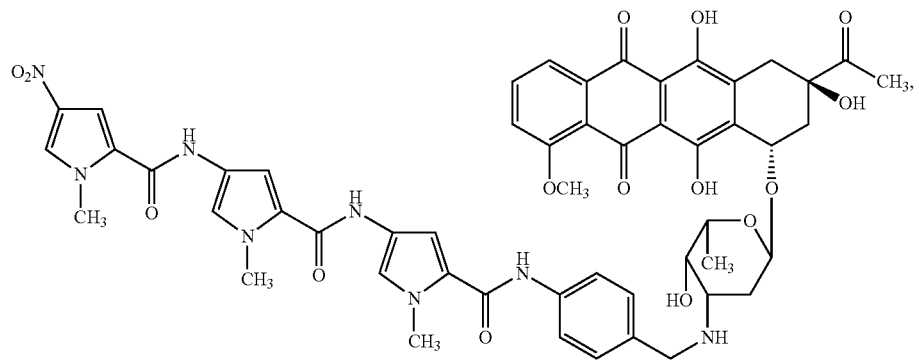
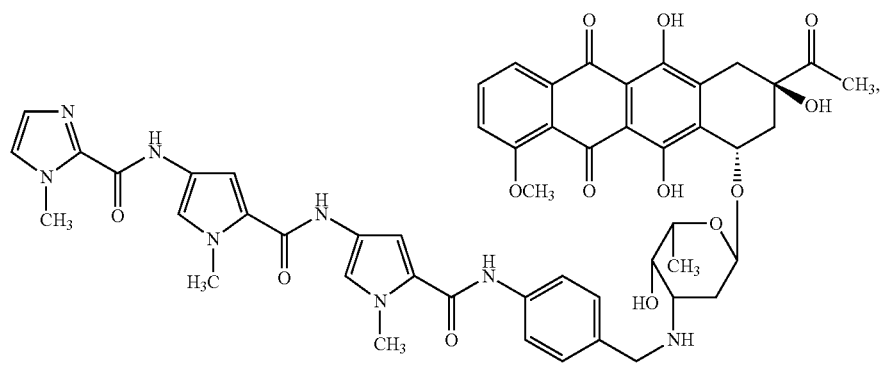
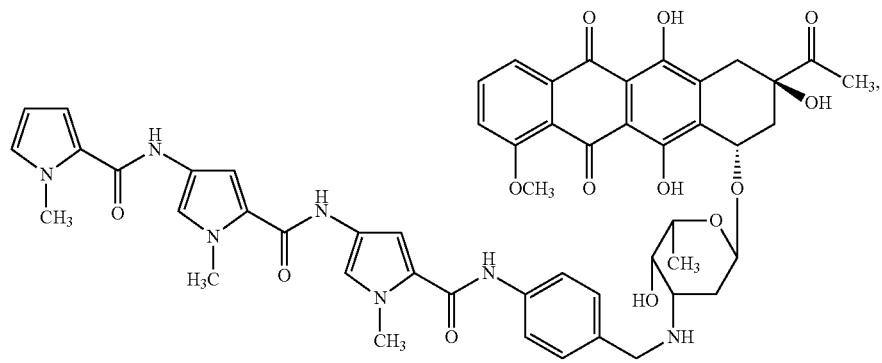
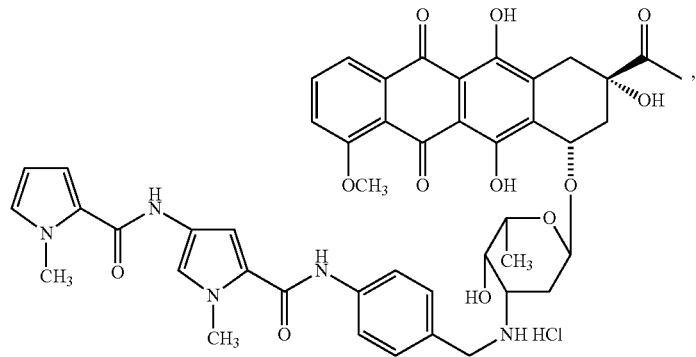

-continued
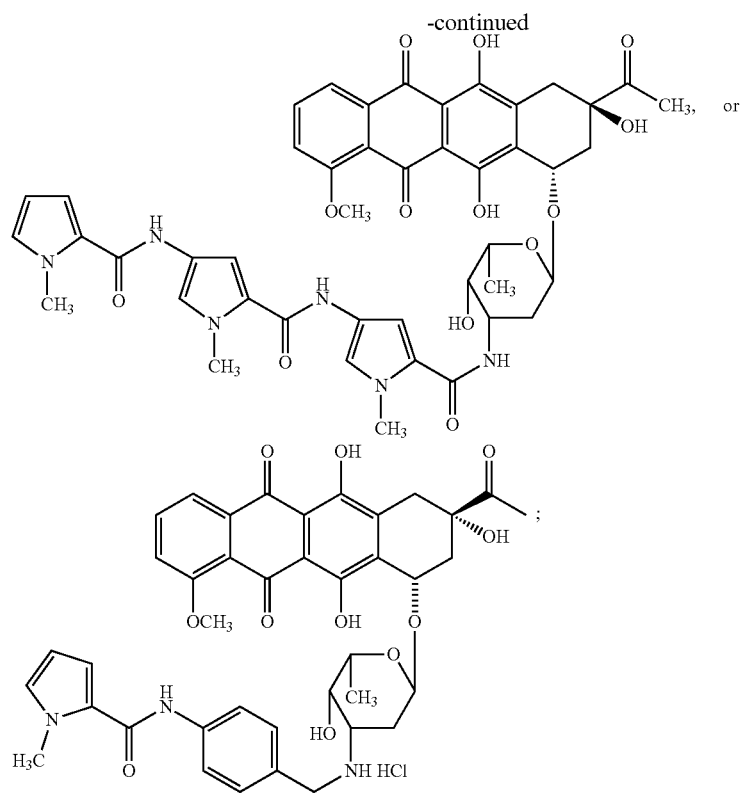
or a pharmaceutically acceptable salt thereof.
19. A pharmaceutical composition comprising:
(a) a compound of claim 1; and
(b) a pharmaceutically acceptable carrier.
20. A method of treating cancer in a patient comprising administering a therapeutically effective amount of a compound of claim 1 to the patient in need thereof.